（12) United States Patent
Klauschen et al.

(10) Patent No.: US 9,558,550 B2
(45) Date of Patent: Jan. 31, 2017

(54) METHOD AND SYSTEM FOR THE AUTOMATIC ANALYSIS OF AN IMAGE OF A BIOLOGICAL SAMPLE

(75) Inventors: Frederick Klauschen, Potsdam (DE); Motoaki Kawanabe, Berlin (DE); Klaus-Robert Mueller, Berlin (DE); Alexander Binder, Berlin (DE)

(73) Assignees: Technische Universität Berlin, Berlin (DE); Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 208 days.

(21) Appl. No.: 14/344,965

(22) PCT Filed: Sep. 14, 2012

(86) PCT No.: PCT/EP2012/068176
§ 371 (c)(1),
(2), (4) Date: Sep. 16, 2014

(87) PCT Pub. No.: WO2013/037983
PCT Pub. Date: Mar. 21, 2013

(65) Prior Publication Data
US 2015/0003701 A1 Jan. 1, 2015

(30) Foreign Application Priority Data

Sep. 16, 2011 (EP) .................................... 11075210

(51) Int. Cl.
G06K 9/62 (2006.01)
G06T 7/00 (2006.01)
G06K 9/46 (2006.01)

(52) U.S. Cl.
CPC ........... *G06T 7/0012* (2013.01); *G06K 9/4642* (2013.01); *G06K 9/4671* (2013.01); *G06K 9/4685* (2013.01);

(Continued)

(58) Field of Classification Search
None
See application file for complete search history.

(56) References Cited

U.S. PATENT DOCUMENTS 7,747,547 B1 * 6/2010 Buturovic ............ G06K 9/6277
435/6.13
8,515,150 B2 * 8/2013 Mangoubi ............ G06K 9/0014
382/133

(Continued)

OTHER PUBLICATIONS

Content-Based Access to Medical Image Collections. Juan Caicedo et al. 2009.*

(Continued)

*Primary Examiner* — Kim Vu
*Assistant Examiner* — Delomia L Gilliard
(74) *Attorney, Agent, or Firm* — The Webb Law Firm

(57) ABSTRACT

Method for the automatic analysis of an image of a biological sample with respect to a pathological relevance, wherein a) local features of the image are aggregated to a global feature of the image using a bag of visual word approach, b) step a) is repeated at least two times using different methods resulting in at least two bag of word feature datasets, c) computation of at least two similarity measures using the bag of word features obtained from a training image dataset and bag of word features from the image, d) the image training dataset comprising a set of visual words, classifier parameters, including kernel weights and bag of word features from the training images, e) the computation of the at least two similarity measures is subject to an adaptive computation of kernel normalization parameters and/or kernel width parameters, f) for each image one score is computed depending on the classifier parameters and kernel weights and the at least two similarity measures, the at least one score being a measure of the certainty of one pathological category compared to the image training dataset, g)

(Continued)

for each pixel of the image a pixel-wise score is computed using the classifier parameters, the kernel weights, the at least two similarity measures, the bag of word features of the image, all the local features used in the computation of the bag of word features of the image and the pixels used in the computations of the local features, h) the pixel-wise score is stored as a heatmap dataset linking the pixels of the image to the pixel-wise scores.

16 Claims, 12 Drawing Sheets

(52) U.S. Cl.
CPC ............ *G06K 9/629* (2013.01); *G06K 9/6292* (2013.01); *G06T 2210/41* (2013.01)

(56) References Cited

U.S. PATENT DOCUMENTS

| 2005/0228591 | A1* | 10/2005 | Hur ..................... | G06K 9/6215 702/19 |
| 2010/0205124 | A1* | 8/2010 | Ben-Hur ............. | G06K 9/6215 706/12 |

OTHER PUBLICATIONS

Combining Low-level Features for Improved Classification and Retrieval fo Histology Images. Juan Caicedo et al. 2010.*
Caicedo at al., "Content-Based Access to Medical Image Collections", Biomedical Image Analysis and Machine Learning Technologies: Applications and Techniques, (Jan. 1, 2009), pp. 1-23.
Caicedo et al., "Combining Low-level Features for Improved Classification and Retrieval of Histology Images", 5th International Conference on Mass Data Analysis of Images and Signals in Medicine, (May 14, 2010).
Yao et al., "Combining randomization and discrimination for fine-grained image categorization". Computer Vision and Pattern Recognition (CVPR), IEEE Conference on Jun. 20, 2011, pp. 1577-1584.
Rasmussen at al., "Visualization of nonlinear kernel models in neuroimaging by sensitivity maps", NEUROIMAGE, (Apr. 1, 2011), pp. 1120-1131, vol. 55, No. 3.
Baehrens, "How to Explain Individual Classification Decisions", Journal of Machine Learning Research, (Jun. 1, 2010), pp. 1803-1831, No. 11.
Liu at al., "What has my Classifier Learned? Visualizing the Classification Rules of Bag-of-Feature Model by Support Region Detection", (Apr. 6, 2012).
Wang at al. "Bag-of-Features Based Medical Image Retrieval via Multiple Assignment and Visual Words Weighting", IEEE Transactions on Medical Imaging, IEEE Service Center, (Aug. 18, 2011), pp. 1996-2011, vol. 30, No. 11, Piscataway, NJ, US.
Uijlings at al., "The Visual Extent of an Object; Suppose We Know the Object Locations", International Journal of Computer Vision, Kluwer Academic Publishers, BO, (May 10, 2011), pp. 46-63, vol. 96, No. 1.
Vedaldi et al., "Efficient Additive Kernels via Explicit Feature Maps", Transactions on Pattern Analysis and Machine Intelligence, IEEE, (Jul. 2011), pp. 480-492, vol. 34, No. 3, Piscataway, USA.
Gehler et al., "Let the kernel figure it out; Principled learning of pre-processing for kernel classifiers", Computer Vision and Pattern Recognition, IEEE Conference on Jun. 20, 2009, pp. 2836-2843.
Wang at al. "Locality-constrained linear coding for image classification", Computer Vision and Pattern Recognition Conference (2010).
Moosmann et al., "Randomized clustering forests for image classification", IEEE Transaction on Pattern Analyses & Machine Intelligence, (Sep. 2008), p. 30 (9).
Cruz-Roa at al., "Visual Pattern Analysis in Histopathology Images Using Bag of Features", Bayro-Corrochano, Eklundh, (2009), pp. 521-528, Springer.
Gemert et al., "Kernel codebooks for scene categorization", European Conference on Computer Vision, (2008).
Varma et al., "More generality in efficient multiple kernel learning", International Conference on Machine Learning (ICML), (2009), p. 134.
Kloft et al., "Lp norm multiple kernel learning", Journal of Machine Learning Research, (Mar. 2011), pp. 953-997, vol. 12.
Yan at al., "Non-sparse Multiple Kernel Learning for Fischer Discriminant Analysis", Proceedings of the 2009 Ninth IEEE International Conference on Data Mining, (2009), pp. 1064-1069.
Yan et al., "Lp norm multiple kernel Fisher discriminant analysis for object and image categorization", Computer Vision and Pattern Recognition, IEEE Computer Society Conference, (2010), pp. 3626-3632.
Cao et al., "Heterogeneous features of machines for visual recognition", ICCV, (2009), pp. 1095-1102.

* cited by examiner

2 Feature Extraction

2-1 Local Feature Extraction (on each image from a set of subimages of one big histo tile)

2-1-1 Compute Regions of Local Feature Extraction
Input: Image from set of subimages of one Big histo tile Examples:
2-1-1-A Grid with varying Step size;
2-1-1-B Biased random sampling (existing method)
But adapted to local statistical Properties of histological stain
(Draws points from probability estimate Of some quantity)

NOT used: SIFT keypoints
(may have impact on applicability Of David Lowe's SIFT patent?!)

2-1-2 Extract local Features
Over points for local feature extraction over pixel-wise Transformation of images (color channels computed from Original color channels)
For each final feature take one fixed scale for below Descriptions
Input: Image from set of subimages Regions from 2-1-1
Output for each image one set of Local features → To 2-2
→ To 2-3

Examples:
2-1-2-A SIFT descriptor
2-1-2-B (pixel) Intensity quantiles
2-1-2-C gradient norm quantiles
2-1-2-D concatenation of intensity quantiles and gradient norm quantiles
2-1-2-E gradient orientation-based Descriptors (SIFT-like)
2-1-2-F. For patent also: histograms instead of above quantiles

Fig. 1A (cont.)

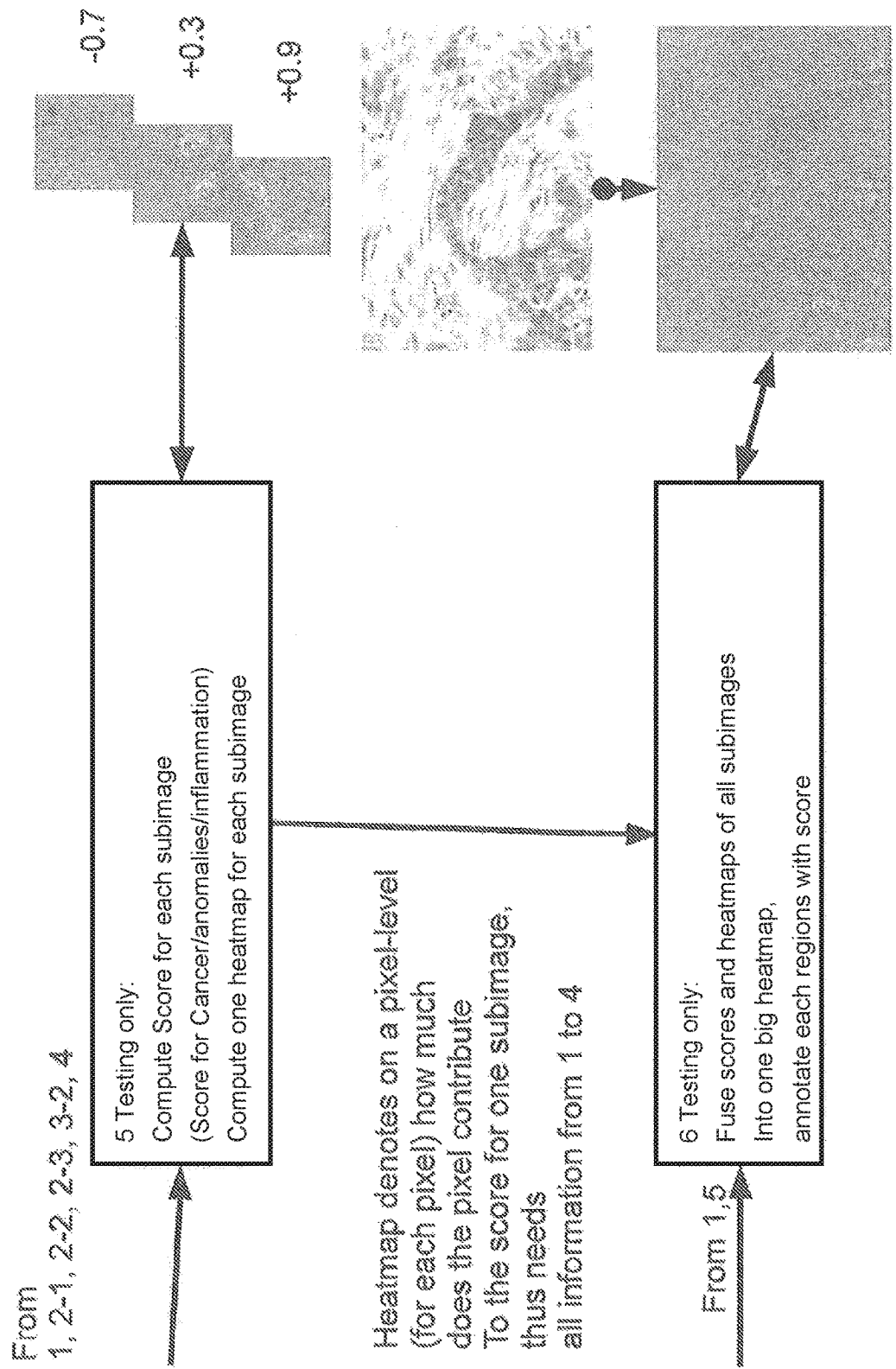

METHOD AND SYSTEM FOR THE AUTOMATIC ANALYSIS OF AN IMAGE OF A BIOLOGICAL SAMPLE

CROSS-REFERENCE TO RELATED APPLICATIONS

This application is the United States national phase of International Application No. PCT/EP2012/068176 filed Sep. 14, 2012, and claims priority to European Patent Application No. 11075210.2 filed Sep. 16, 2011, the disclosures of which are hereby incorporated in their entirety by reference.

SUMMARY OF THE INVENTION

In the following an embodiment of the method is described. The task described herein is the generation of a local scoring (i.e. some form of metrics) for the detection of regions in an image which are suspicious of cancer. The efficient analysis of medical images for cancer cell detection is an important application, but the method can also be used of the analysis of other images related to biological samples, like PET scans of the brain.

Other sources of images can originate from an analysis of inflammated tissue; CT scans, MRI scans; combination images from the above such as PET+MRI fusion. But biological sample also include samples of immobilized body liquids such as blood, cerebrospinal fluid, urine, bile, ejaculate, saliva, blood serum, lymph, mucus, peritoneal fluid, pleural fluid, gastric juice, tears, vaginal secretion The automatic generation of the score can be an important tool for the doctor in assessing a large number of images.

BRIEF DESCRIPTION OF THE DRAWINGS

Embodiments of the invention are shown in the figures.
Embodiments of the invention are shown figures.

DETAILED DESCRIPTION OF THE INVENTION

Figure 1:
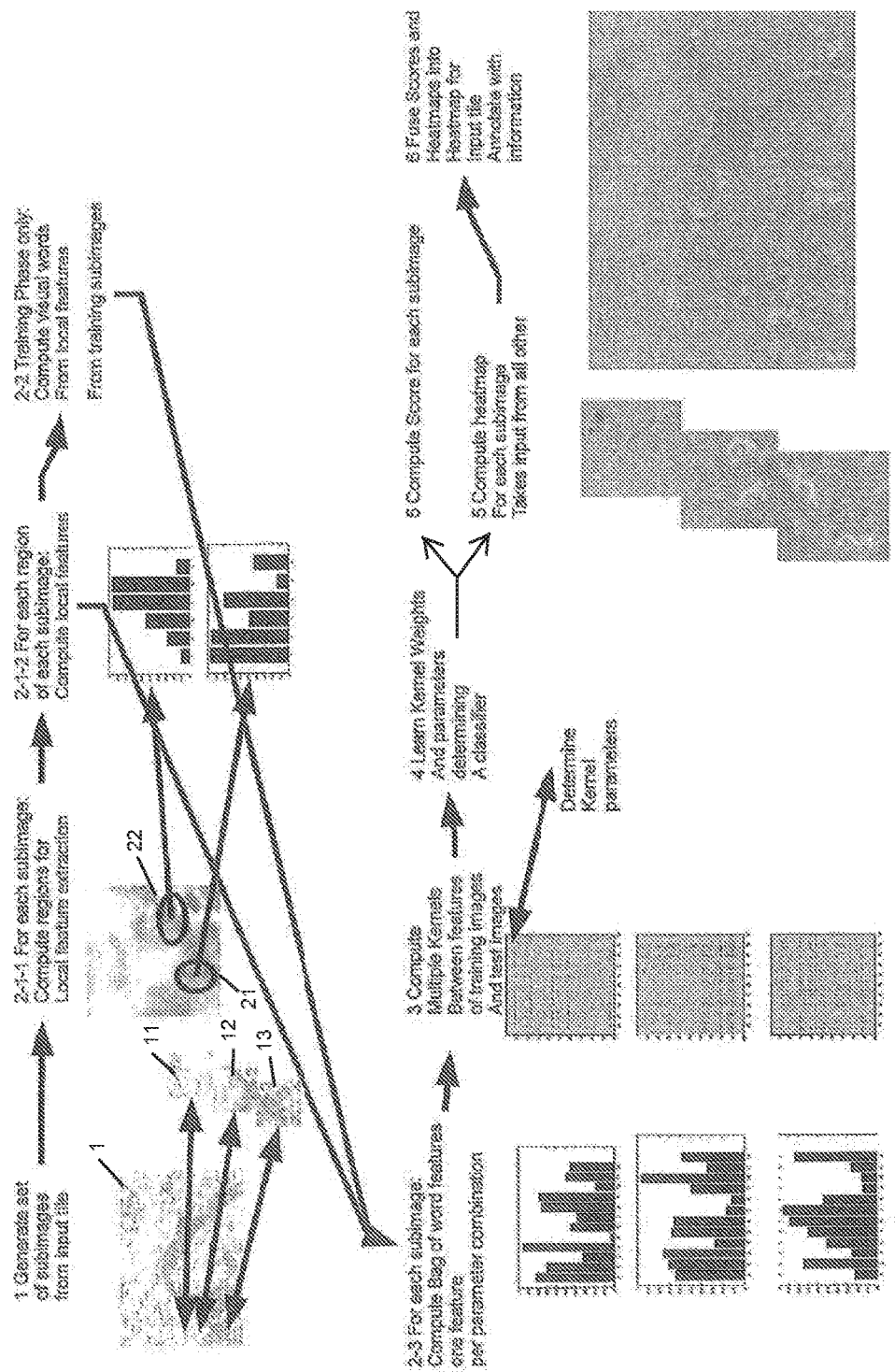
FIG. 1 shows an overview of an embodiment for the processing of an image.
Figure 1A:
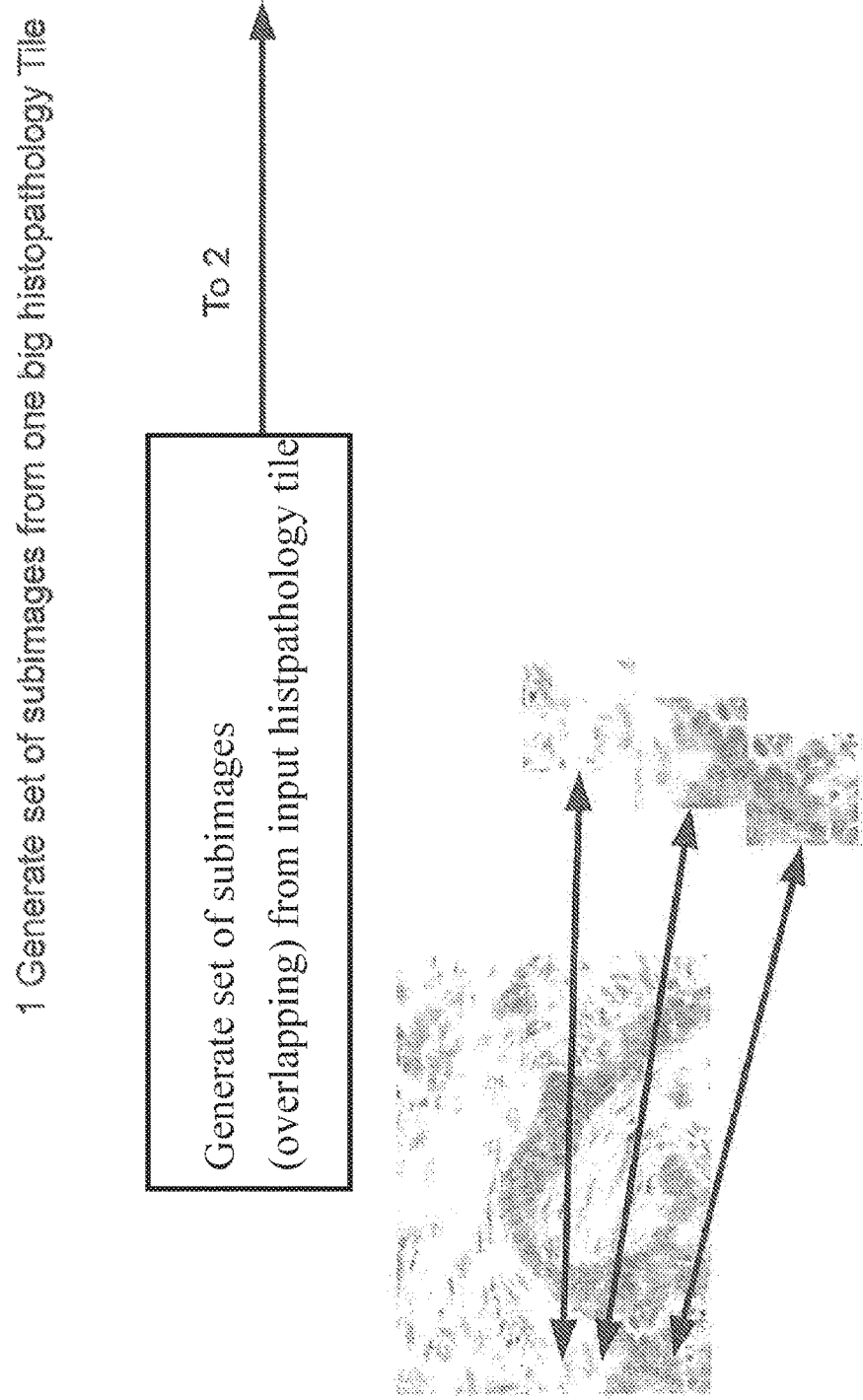
FIG. 1A shows a more detailed overview of an embodiment of the processing of an image.
Figure 1A:
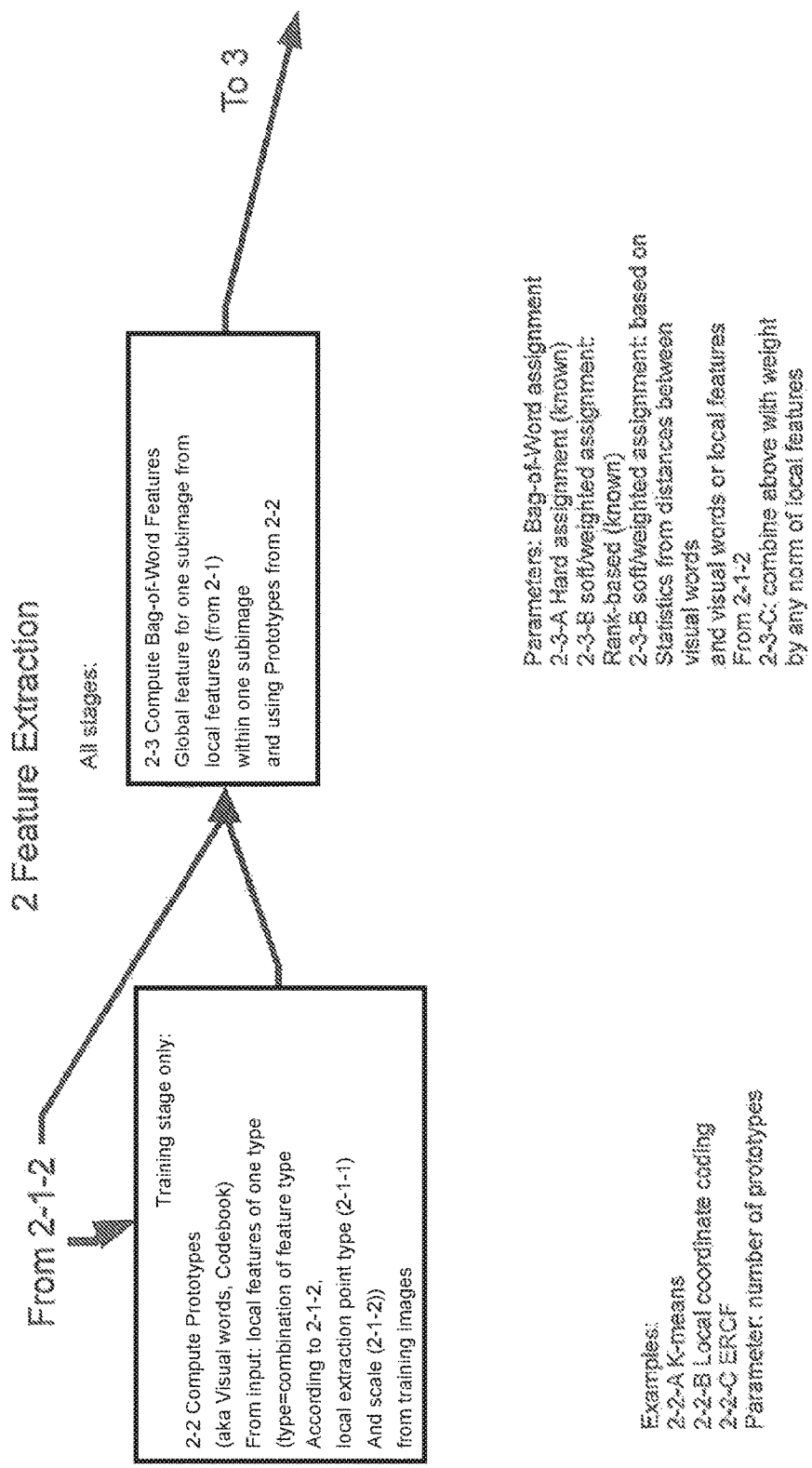
Figure 1A:
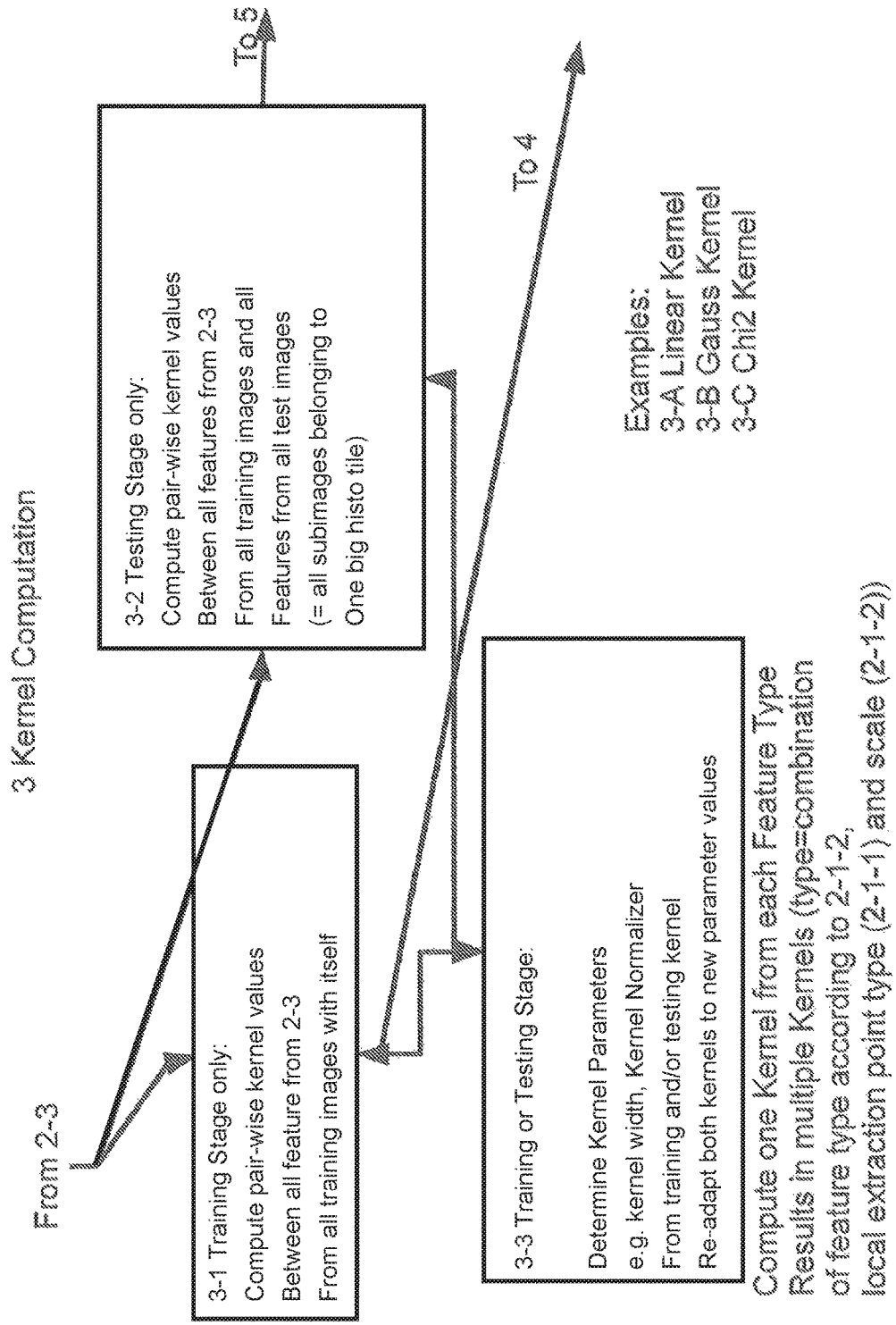
Figure 1A:
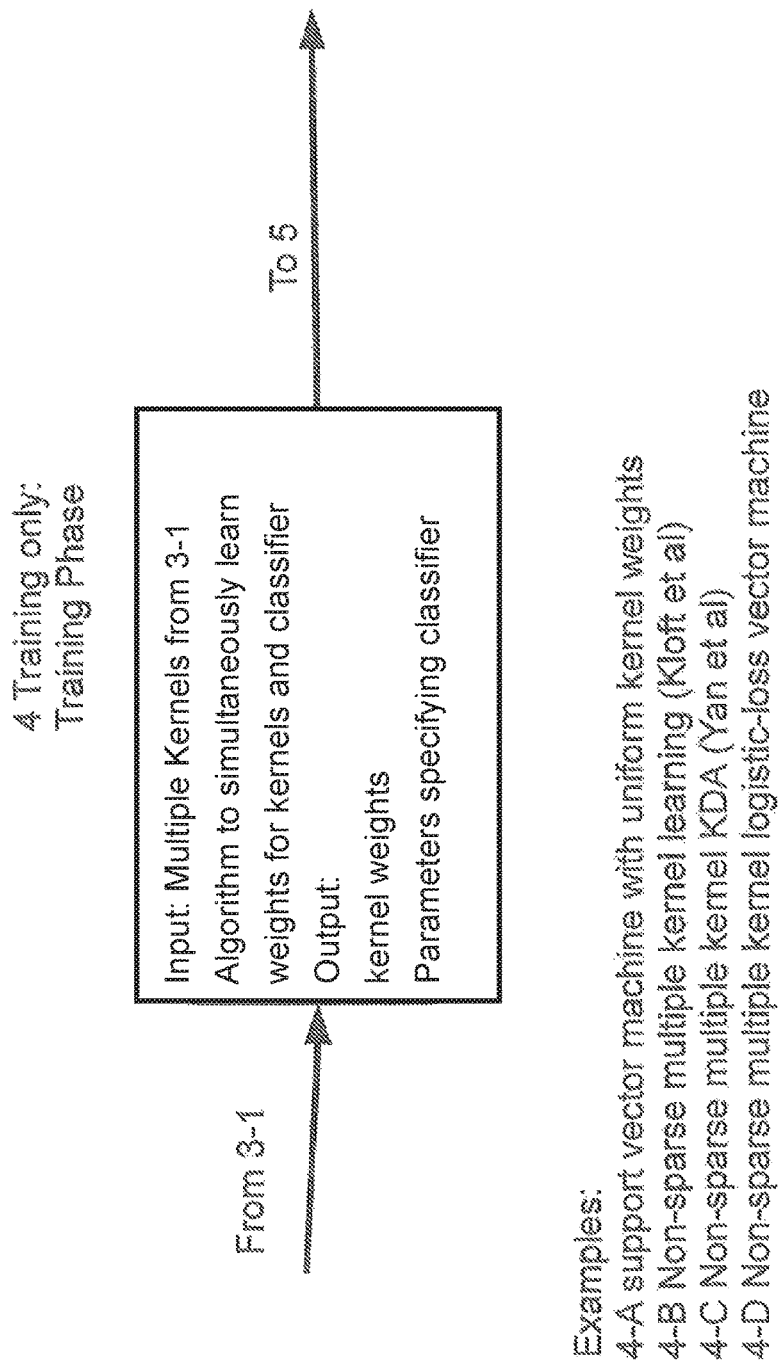

Starting with a histological section of a tissue sample, a digitized image is prepared (see FIG. 1). Usually the tissue samples are taken from the body and cut into thin slices, so that single cells can be made visible. Furthermore, the tissue samples can be stained, e.g. with Haematoxylin, which stains different cell types differently. The biological sample is then photographed under a microscope with appropriate magnification to yield a color image of the tissue sample.

The digitized image is made up from pixels in a way known in the prior art. The method uses the digitized image, i.e. the pixels for further analysis, in particular the generation of the score for a region of the image denoting whether cancer cells are present or not.

In the presented embodiment, the score is normalized into the range [−1 1]. A positive score in [0 1] indicates presence of cancer within a region in the image, with 1 being the maximal value of certainty. A negative score in [−1 0] indicates the absence of cancer cell, with −1 being the maximal value of certainty.

The score for a region can be annotated into an output image which is then used in further analysis. Alternatively, different color shades overlaid over the original image can be used to visualize the certainty of the presence of cancer. E.g. a red semi-transparent overlay on the original image can indicate a higher certainty of the presence of cancer.

However the annotation of a region as a whole with the certainty score or coloring the region according to the score has one disadvantage. Typically the score is computed for a region having a size such that the region contains multiple cells. The score is constant for that region. While it has advantages to compute the score over a larger region having multiple cells with respect to robustness of the score, the contributions of parts of the region to the score, like particular cells, cannot be seen in such kind of coloring of the image.

But the embodiment of the method offers a further advantage, since it allows an analysis of how much each pixel contributes to the score over a certain region of the image containing the pixel. This is achieved by a different color coding (see FIG. 6).

The output image shows the original input image converted into shades of gray with overlaid colors varying in shades from red to blue. An increasing red hue of a pixel denotes that this pixel contributes evidence for presence of cancer; an increasing blue hue denotes that this pixel contributes evidence against the presence of cancer. A green hue denotes low evidence for either possibility.

In following the different steps in obtaining the analysis will be described. The embodiments of the methods herein can be used in a system, e.g. an automated medical device, to analyze biological samples. Even though in the following a method is described it is understood that the method can be embedded in software and/or hardware to be used as a system.

In FIG. 1 under section 1 a digitized image 1 of a biological sample is shown. From this image subimages 11, 12, 13 are generated which preferably overlap each other. The overlapping has the effect that certain features in the image are not always confined e.g. to a border of one of the subimages 11, 12, 13. A subimage is an ordered set of subimage channels, a subimage channel is an ordered set of pixels.

In principle it is possible to apply the following process to one image alone, without generating subimages 11, 12, 13. Using subimages 11, 12, 13 has certain computational advantages, so in the following the use of subimages 11, 12, 13 will be described.

The automatic generation of subimages 11, 12, 13 can be performed based on a fixed format along a given grid. In principle other methods can be used such as adaptive subimage sampling. In this method at first the format of potential subimage 11, 12, 13 is fixed. Then each region of the image that satisfies the fixed format gets assigned a score. The score can be a function of the color values of pixels of that region in a new color channel which is generated by an application of an arbitrary function on the color channels of the original image. A subimage 11, 12, 13 is created if the score is above a certain threshold value.

Alternatively, all these scores are normalized, so that they are non-negative and sum up to one. Each score belongs to one region in the image which satisfies the fixed format and therefore, can be used as subimage 11, 12, 13. The normalized scores are discrete probability distributions over regions. In the alternative procedure subimages 11, 12, 13 are created by drawing regions from this discrete probability distribution.

This procedure has the advantage that e.g. fat tissue or empty spaces turn out very bright. Stronger colored zones are of higher interest since there cells, cell nucleus or other colored objects of interest can be found. Consequently those should be covered more detailed by subimages 11, 12, 13. One reason for using subimages is the separate processability which allows computational parallelization on CPU or GPU clusters.

Another reason for using subimages is that the size of the image or subimage used to compute the bag of word features has substantial influence on the classification performance of the system in the sense if error rates. The size of the subimages can be chosen sufficiently large in order to be able to recognize certain structures relevant for the detection of cancer such as cell growth patterns which are typically visible from some size on. Larger subimages improve the robustness of the bag of word features used in the method here against noise. On the other hand considering too large subimages may result in overlooking smaller cancerous structures embedded in otherwise normal tissue. As explained later a bag of words feature is computed from many local features. If the subimage or image is too large then the local features computed over regions corresponding to normal tissue will dominate in the resulting bag of words feature which explains why smaller cancerous structures embedded in otherwise normal tissue can be overlooked in too large images or subimages.

Now regions 21, 22 are calculated for each subimage 11, 12, 13 which then can form the basis for further processing.

In FIG. 1 under section 2.1.1 it is shown that for each subimage 11, 12, 13 regions are calculated for the extraction of local features for that region 21, 22. A local feature is a function of the region, i.e. a set of numerical values describing certain properties of the region, a region is a set of pixels.

A number of input parameters are required for the definition of a region 21, 22. In the following some examples are described. A circle can be defined by the position of a basis pixel (i.e. the center of the circle) and the radius measured in pixels. An elliptic region (see FIG. 1 section 2.2.1) can be defined by the length of the long and the short axis and the position of a basis pixel for the center or a focal point of the ellipse. A quadratic region can be described by a basis pixel location and a side length. Similarly other geometric shapes can be used to define a region 21, 22.

In general the region can be defined by the region's shape and the region size. Furthermore, the number of regions 21, 22 within a subimage 11, 12, 13 is an input parameter for determining the region. It is possible to automatically choose the number, size and/or shape of the regions 21, 22 adaptively, e.g. proportionally to the number of the pixels in the subimage 11, 12, 13.

In the following we assume that the region shape is such that it can be identified by a basis pixel, that means we specify a pixel and this allows to allocate uniquely the corresponding region.

Given the input parameters, it is possible to calculate different regions 21, 22 in the subimages 11, 12, 13. In the following three different embodiments are described which can be used to define basis pixels (e.g. the center or corner of the region) for the regions.

1. A biased sampling approach requires the computation of a probability distribution over pixels from the subimage 11, 12, 13. For example the distribution is proportional to the grey values of a pixel.

One possible example for a biased random sampling involves a subimage of grey values which is computed from the subimage. The grey values are scaled such that they lie in the interval [0,1] for each pixel. This grey-value subimage can be turned into a probability map by dividing each pixel value by the total sum of the grey values in the grey subimage. This probability map is a two-dimensional matrix, each entry is a non-negative value and corresponds to one pixel and the sum of its values sums up to one. Thus it is a discrete probability distribution over pixels and given a fixed number N, N basis pixels can be drawn from it. Each of the pixels corresponds uniquely to a region.

2. A grid sampling approach selects pixels by defining a regular grid, e.g. a honeycomb pattern, a triangle pattern, a quadratic grid etc. The pixels which lie closest to the corner points of the overlaid grid are selected.

3. An overlapping grid sampling approach is a variation of the grid sampling approach. The regular grid is used as well to select pixels, but the pixels are chosen so that the corresponding regions 21, 22 do overlap. It is an advantage that the overlapping of local features captures more information.

The result of this process step is a set of regions 21, 22 in the subimage 11, 12, 13. Each of the regions is defined as a set of pixels. The regions 21, 22 in the subimage 11, 12, 23 can have different shapes and/or sizes.

Figure 2:
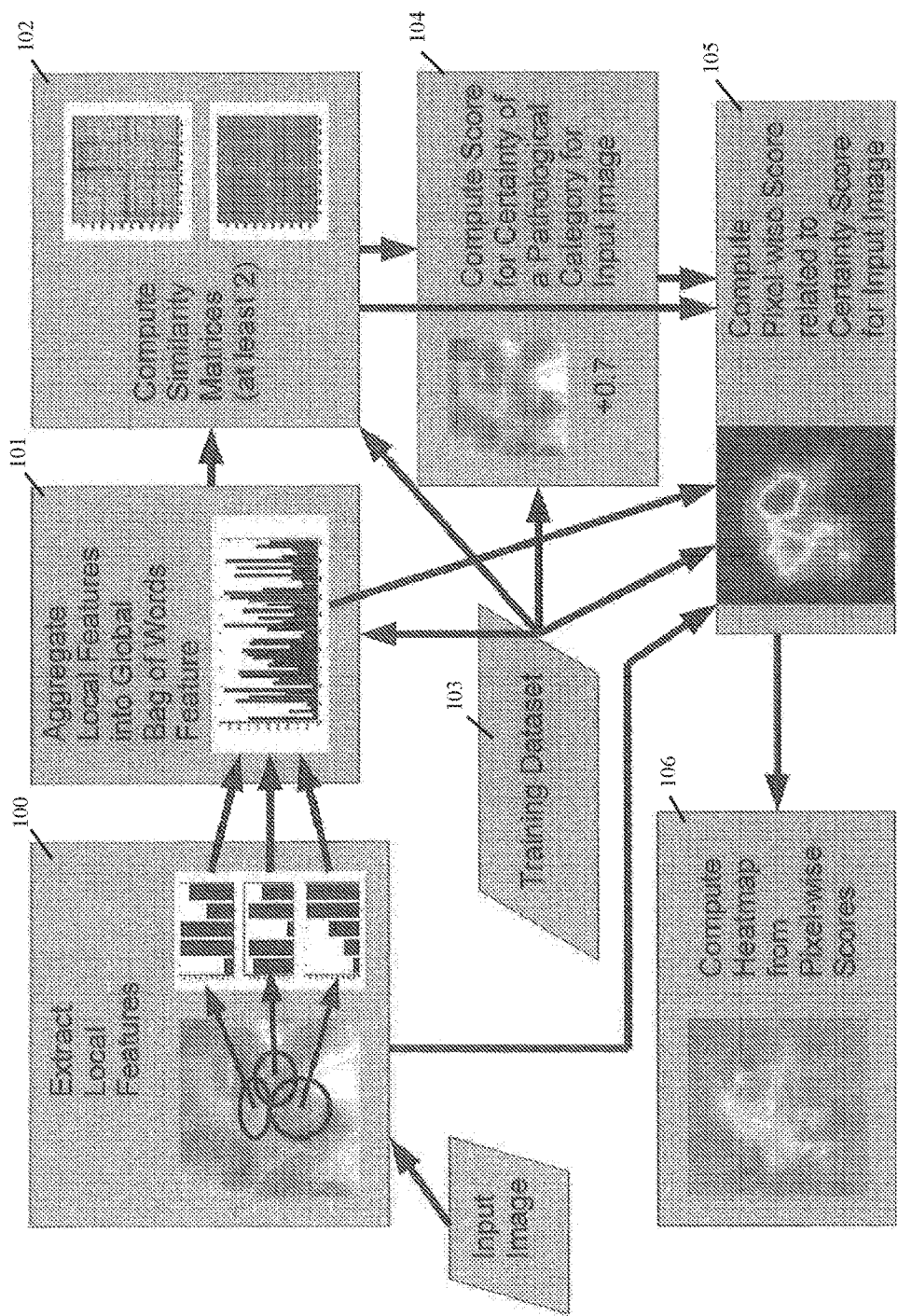
FIG. 2 shows a flowchart of an embodiment for the testing procedure.

Having defined regions 21, 22 it is possible to characterize them by calculating local features, i.e. some numerical characterization of the region 21, 22 (see FIG. 1 section 2.1.2 and FIG. 2 process step 100).

The input parameters for the local feature calculation are a region 21, 22, i.e. a set of pixels, as defined in the previous process step and—if necessary—some parameters for the algorithm (e.g. the quantile parameters for a quantile based local feature).

The output of the local feature computation is an ordered set of real numbers (e.g. In form of a vector, depicted in FIG. 1 section 2-1-2 and FIG. 2, process step 100). Furthermore, parameters specifying the position, extent and geometry of the region can be computed, which will be required, if a heat map (see below) will be generated.

In the following a number of local features and their methods of computations are discussed. The methods can be used individually or in any combination.

Each of the local features mentioned in the following can be computed over a set of color channels which are computed from the original color channels by applying a transformation on the original color channels. One simple example for such a transformation is the function which computes for each pixel the grey value and the blue value from the pixels of a RGB image that is used as input.

1. One known method for computing local features in an image is the gradient-based descriptor underlying the scale-invariant feature transform (SIFT).

2. A pixel-wise intensity quantile estimator vector method utilizes the intensity of a pixel-wise function of the subimage 11, 12, 13. The quantile estimator vectors are sets of quantile estimators for varying quantile values e.g.: 0: minimum value, 0.5: median value and 1 maximum value.

3. A pixel wise gradient norm quantile estimator vector method uses gradient norms computed from the intensity values of a pixel-wise function of the subimage 11, 12, 13. From the set of gradient norms over a region a set of quantile estimators corresponding to various quantile values are computed e.g.: 0: minimum value, 0.5: median value and 1 maximum value computed by a pixel wise intensity quantile estimator vector method.
4. A method using histograms of pixel-wise intensities.
5. A method using histograms of pixel-wise gradient norm.

Furthermore, local features can be computed from gradients at pixels over regions selected.

The preceding process steps are used in the case of testing real images 1 but also in a training procedure for the method.

The training procedure comprises a process step (section 2.2 in FIG. 1) which uses the output of the local feature calculation (section 2.1.2 in FIG. 1) to compute visual words (i.e. an analogue term from the text-based bag-of-words approach, only applied to local features extracted from images) from the local features extracted from the subimages 21, 22. This can be understood as a computation of prototypes. Examples for this computation are K-Means, local coordinate coding (Wang et al., Locality-constrained linear coding for image classification, Computer Vision and Pattern recognition Conference (CVPR), 2010) and ERCF (Moosmann et al., Randomized clustering forests for image classification, IEEE Transaction on Pattern Analysis & Machine Intelligence, 30(9):1932-1646, September 2008)

Visual words are a set of points which are chosen in the space of local features (e.g. "Visual Pattern Analysis in Histopathology Images Using Bag of Features" by Cruz-Roa et al. in Bayro-Corrochano, Eklundh (Eds.), CIAPR 2009, LNCS 5856, pp. 521-528, 2009, Springer.)

The next process step (section 2.3 in FIG. 1) is common to training and testing alike. For each subimage 11, 12, 13 a bag of words analysis is performed on the local features from the subimages 11, 12, 13.

The visual word obtained before (section 2.2. In FIG. 1) are used for all bags of words to be computed. Furthermore, the process step (section 2.3 in FIG. 1) requires parameters for the algorithm such as parameters defining a mapping function, examples of which will be described below.

A bag of word feature can be represented as an ordered set of real values. Each entry in the set corresponds to one visual word from the set of visual words. The computation of a bag of words feature is composed from two steps.

At first, each local feature is mapped onto an ordered set of real values. Each entry in this set corresponds to one visual word. The number of elements in the ordered set is equal to the number of visual words.

Then, all these ordered sets coming from different local features are aggregated into one ordered set which constitutes the BoW feature.

The mapping of a local feature onto an ordered set is usually based on distances (e.g. $l_2$ or chi2) of the local feature from a subimage 11, 12, 13 to the visual words. In textual analysis TF-IDF (term frequency-inverse document frequency) is a well known mapping scheme. In Computer Vision—as it is the case in this embodiment—typically one has a notion of distance between the local features as additional information so that more elaborate weighting schemes such as soft codebook mapping are applicable.

Each of the ordered sets is then aggregated into one ordered set of real values which is the final BoW feature and has the number of dimensions equal to the number of visual words.

The aggregation can be achieved by summing up the ordered sets of real numbers element-wise separately over all local features, i.e. not summing up different elements of the ordered set but summing up each element separately over all local features—see equation (0) below.

The input is a set of local features $\{l_1, \ldots, l_N\}$ belonging to one subimage and a mapping scheme $\{m_d, d=1, \ldots, V\}$ which maps each local feature onto the d-th entry in the ordered set (the mapping scheme contains the visual words implicitly, typically the mappings of the weighting scheme across histogram dimensions d are related to each other)

The output is a bag of word feature x, with $x_d$ is its value in the d-th dimension. This can be expressed formally as $$x_d = \sum_{i=1}^{N} m_d(l_i), \tag{0}$$

where $l_i$ is a local feature and $m_d$ is the weighting scheme, a mapping of a local feature onto histogram dimension d which depends on the set of visual words. This yields one global bag of word feature for each subimage. The features can be normalized, e.g, multiplying x with a function of x.

In the following some methods for the assignment of bag of words are described.

1. In a bag of words soft mapping approach the mapping of a local features onto an ordered set of real values is performed such that for each set of local features which belongs to a subimage 11, 12, 13 there exists at least one local feature such that the mapping of this local feature is non-zero in at least two elements of the ordered set which is the result of this mapping. (in mathematical terms: for each subimage 11, 12, 13, exists one $l_i$ and exists at least two mapping dimensions d such that $m_d(l_i) > 0$.

In contrast, a hard mapping approach (such as TF or TF-IDF) maps each local feature on exactly one element of the ordered set which is the result of this mapping. The next two alternatives refer to soft mapping procedures.

2. A bag of word soft mapping "rank" approach uses additionally an exponent parameter and computes the ranks of distances of a local feature to the set of visual words. The exponent parameter specifies the rate of decay of the numerical value of the mapping as a function of the rank. This method avoids oversmoothing by guaranteeing a sufficient decrease of mapping values as functions of ranks of distances. Be $Rk_d(l)$ the rank of the distance of the local feature to the visual word which is represented by dimension d in the bag of words feature.

The mapping of a local feature given a set of visual words is performed follows:

$$m_d(l) = \begin{cases} p^{-Rk_d(l)} & \text{if } Rk_d(l) \leq N \\ 0 & \text{otherwise} \end{cases}$$

The mapping value for a dimension corresponding to a visual word is proportional to the exponent parameter p power the rank of this visual word $Rk_d(l)$ with respect to the distances of all visual words of the local feature. The rank is computed with respect to the distance between the local feature and all the visual words. The mapping value is set to zero if the rank exceeds a threshold N.

3. The bag of word approach "soft mapping including an adaptive exponent" uses the local feature l to compute distances of that local feature to the visual words. It computes a parameter σ defining the rate of decay of the numerical value of the mapping as a function of the distances between the local feature and each of the visual words in an adaptive manner.

Additional input parameters are the number of nonzero entries N in the mapping $m_d(l_i)$ and a positive mapping value factor $v \in ]0,1[$ for the smallest nonzero entry, which is necessary for the adaptive computation of the parameter defining the rate of decay. The mapping values for dimensions corresponding to all other visual words except for the N nearest visual words are then set to zero. Be $w_d$ the visual word corresponding to dimension d in the bag of word feature.

The mapping of a local feature given a set of visual words proceeds as follows:

$$m_d(l) = \begin{cases} \dfrac{\exp(-\sigma(l)\text{dist}(l, w_d))}{\sum_{(v \in V | \text{Rank}(\text{dist}(l,v)) \leq N)} \exp(-\sigma(l)\text{dist}(l, v))} & \text{if Rank}(\text{dist}(l, w_d)) \leq N \\ 0 & \text{otherwise} \end{cases}$$

The mapping value for a dimension corresponding to a visual word is a non-increasing parameterized function of the distance between the local feature and the visual word.

One example for a mapping value is the exponential of the negative distance where the distance is multiplied with a scale parameter.

The parameter σ(l) is chosen adaptively such that the mapping value for the nearest visual word relative to the given local feature is 1/v times larger than the mapping value for the N-nearest visual word where v is the mapping value factor from above which gets used in the equation defining σ(l) below Be $\text{dist}_1(l) = \min_{\{x \in V\}} \text{dist}(l,v)$ and $\text{dist}_k(l) = \text{dist}(l,v_0)$ such that $v_0$ yields the K-th smallest distance within the set of distances between the local features l and the visual words. Then the parameter σ(l) is chosen as $$\sigma(l) = \begin{cases} \dfrac{\ln(v)}{\text{dist}_1(l) - \text{dist}_k(l)} & \text{if } \text{dist}_1(l) - \text{dist}_k(l) < 0 \\ 1 & \text{otherwise} \end{cases}.$$

Note that ln(v) is negative due to $v \in ]0,1[$.

The soft mapping smoothes the mapping values of a local feature to neighboring visual words. It also improves the classification performance. This method avoids oversmoothing by guaranteeing a sufficient decrease of mapping values but adapts to local statistics in the space of local features.

One of advantages of the soft mapping approach is that it smoothes the mapping values of a local feature to neighboring visual words and it improves classification performance. See also Gemert et al. "Kernel codebooks for scene categorization", European Conference on Computer vision, 2008 for a discussion of soft mapping.

Kernel Computation

Figure 3:
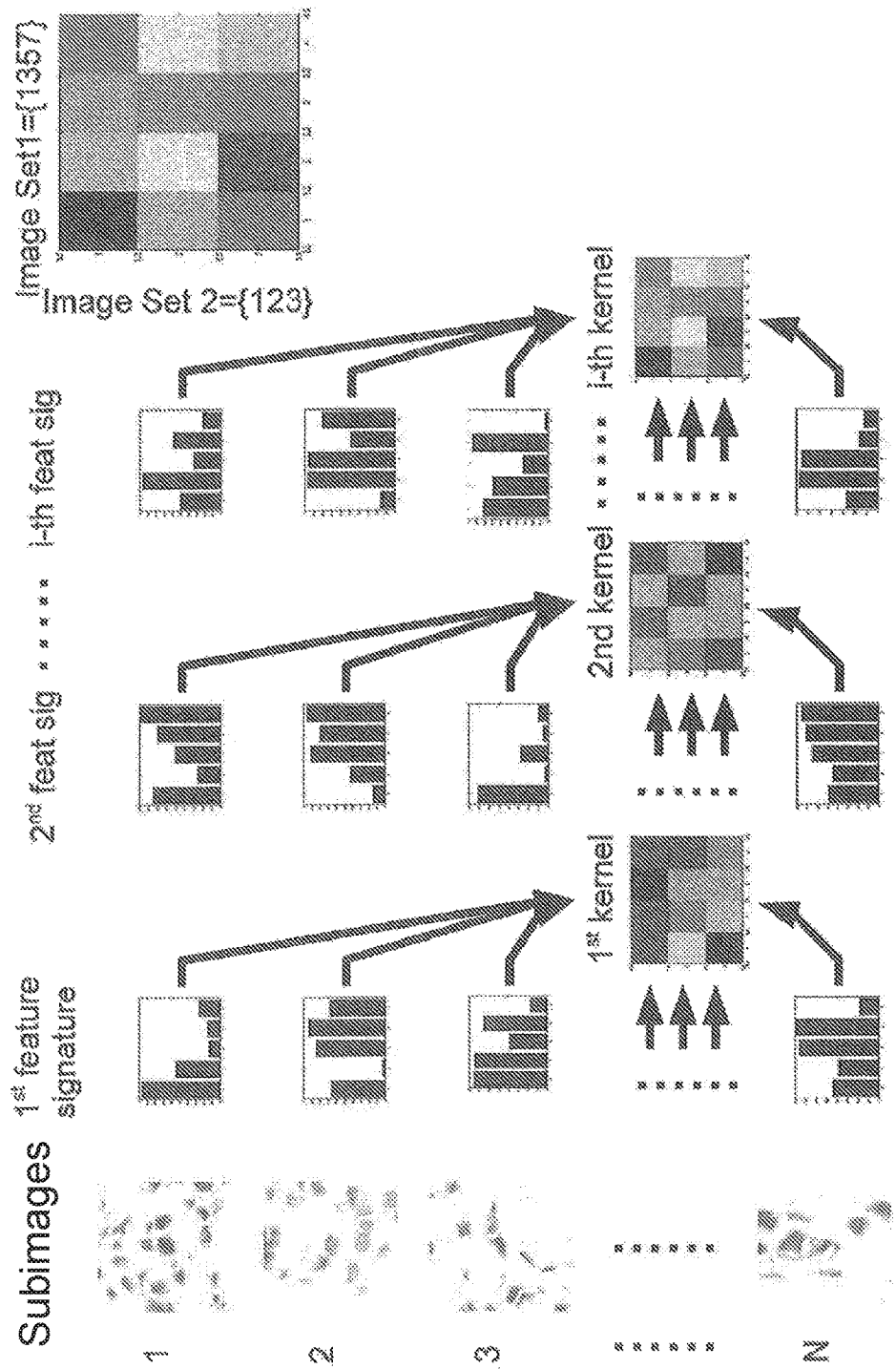
FIG. 3 shows an embodiment of a computation of a kernel.
Figure 4:
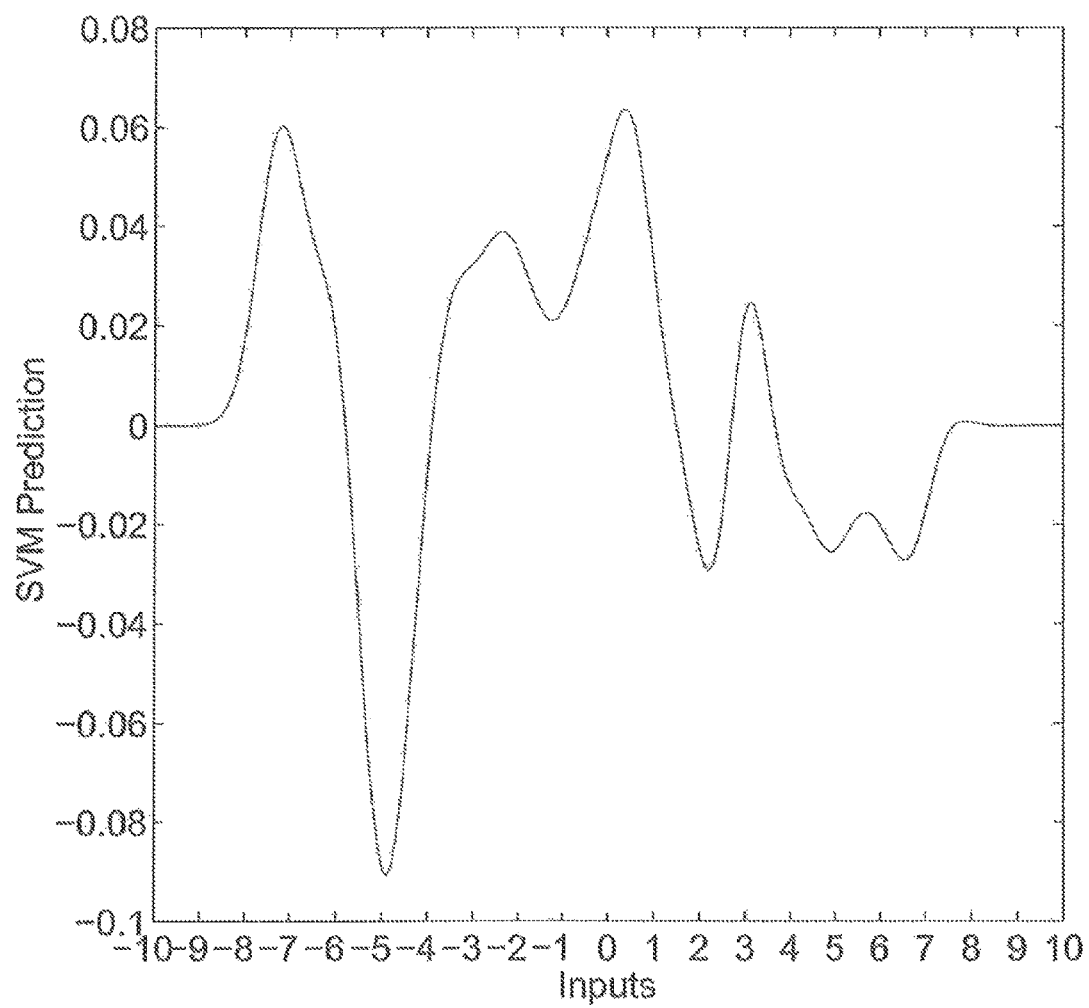
FIG. 4 graphical depiction of a SVM prediction function over one-dimensional inputs using RBF kernels.

After the extraction of the local features and aggregation into global features, kernels needs to be computed (see FIG. 3).

As can be seen in FIG. 3, for each subimage 11, 12, 13 (in FIG. 3: rows 1, ..., N) L global features are known (in FIG. 3 columns 1, ..., L).

Now L kernel matrices are computed (i.e. L separate matrices for testing and L separate matrices for training) from the L global features, as described below.

A kernel matrix is a similarity matrix between two sets of features corresponding to two sets of images, in our case subimages 11, 12, 13. Each entry in the matrix corresponds to a numerical value for similarity between two features, one from the left hand side set (i.e. row set) corresponding to one image and one from the right hand side set (i.e. column set) corresponding to another image:

$$(x_l, x_r) \rightarrow k(x_l, x_r) \tag{1}$$

The function k in equation 1 is called kernel function.

The sets of subimages 11, 12, 13 used to extract features vary between training and test stage. For this reason the sets of features vary between training and test stage.

A kernel matrix has an additional requirement: when the left hand side set and the right hand side set are the same, then the resulting matrix has to be non-negative definite, that means all eigenvalues of the matrix are non-negative.

For each subimage 11, 12, 13 a fixed number L of feature vectors has been computed in the previous steps. Each feature vector has been computed with known fixed set of feature parameters. We call this complete set of feature parameters which do not depend on the input image but are necessary for being able to compute a feature a feature signature.

It can be assumed without loss of generality that the features for each image are ordered in the same manner across all subimages 11, 12, 13: that means that the i-th feature ($i \in \{1, ..., L\}$) has been computed by the i-th feature signature for every subimage 11, 12, 13.

This ordering is depicted in FIG. 3. Then multiple (i.e L) kernels are computed. For computation of the i-th kernel two sets of images are defined taking the i-th feature vectors from each image of both sets. The sets of subimages 11, 12, 13 are different in training and testing stage.

In the following training subimages 11, 12, 13 are images for which manual annotation is available denoting the presence and extent of cancer. In the case of analyzing other problems the type of manual annotation is replaced accordingly, for example, in case of automatic analysis of inflammation of tissues the manual annotation is about the presence and extent of inflammation cues in an image.

A training set of subimages 11, 12, 13 has to be obtained once for the classifier training during the training phase.

In the following testing subimages 11, 12, 13 are images for which a result according to the algorithm as a whole is to be predicted.

Since two different sets of kernel matrices are generated for testing and training, the computation is described below.

Training Stage

Before subimages 11, 12, 13 (or images) can be tested by an embodiment of the method, the method needs to be trained. This requires a kernel matrix to be computed between subsets of the bag of word features computed from training subimages 11, 12, 13.

Input: Left hand side set for the i-th kernel matrix: i-th feature of a subset of the set of all training subimages 11, 12, 13 (Number of training subimages 11, 12, 13 used for kernel computation: Quantity G)

Right hand side set for the i-th kernel matrix: i-th feature of the same set as the left hand side.

Output: i-th training kernel matrix of format G×G.

The mapping is done according to equation 1 using a kernel function. For examples of kernel functions see equations (2) to (7) below.

Testing Stage

Input: Left hand side set for the i-th kernel matrix: t-th feature of a subset of the set of all training images or subimages (Number of training subimages 11, 12, 13 used for kernel computation: quantity G)

Right hand side set for the i-th kernel matrix: i-th feature of all testing subimages (Number of testing subimages 11, 12, 13 used for kernel computation: quantity N)

Output: i-th testing kernel matrix of format G×N.

The mapping is done according to equation 1 using a kernel function. For examples of kernel functions see equations (2) to (7) below. For computing the i-th kernel the same kernel function has to be used during training and testing phase, however the kernel function can vary across feature/kernel indices (i.e. the kernel function for the first feature/kernel can be different from the one for the second).

Kernel Functions Used for Equation (1)

In the following some embodiments for kernels which can be used in connection with the above given equation (1).

1. A Linear kernel as defined by $$k_p(x_l, x_r) = p \langle x_l, x_r \rangle \quad (2)$$

where $\langle \cdot, \cdot \rangle$ denotes any scalar product on the vector space $R^d$, for example the canonical scalar product which gives rise to the Euclidean norm there. p is a kernel normalization parameter.

2. A generalized exponential kernel as defined by $$k_{w,p}(x_l, x_r) = p \exp(-w d((x_l, x_r))) \quad (3)$$

The generalized exponential kernel has two parameters: the normalization parameter p and the kernel width w. d is a distance function such that the resulting kernel matrix is positive definite in the sense defined above. Examples for this type of kernel function are the below given as Gaussian and chi2 kernel functions defined below.

3. A Gaussian kernel is defined by $$k_{w,p}(x_l, x_r) = p \exp(-w \|x_l - x_r\|_2^2) \quad (4)$$

where $\|x_l - x_r\|_2^2$ is the square of the Euclidean norm. The Gaussian kernel has two parameters: the normalization parameter p and the kernel width w.

4. A chi2 kernel is defined by $$k_{w,p}(x_l, x_r) = p \exp\left(-w \sum_{d \in \{1,\ldots,D\} | x_l^{(d)} + x_r^{(d)} > 0} \frac{(x_l^{(d)} - x_r^{(d)})^2}{x_l^{(d)} + x_r^{(d)}}\right) \quad (5)$$

where $x^{(d)}$ denotes the d-th component of the vector x. In case of all components of both vectors being zero the kernel value is equal to p.

5. A polynomial kernel is defined by $$k_{w,p,t}(x_l, x_r) = p(\langle x_l, x_r \rangle + w)^t \quad (6)$$

where t is the degree of the kernel.

6. A histogram intersection kernel is defined by $$k_{w,p}(x_l, x_r) = p \sum_{d=1}^{D} \min(x_l^{(d)}, x_r^{(d)}) \quad (7)$$

where x(d) denotes the d-th component of the vector x.

Adaptive Estimation on Kernel Parameters

The kernels which have been listed above have at least one parameter which is adapted during the process, e.g. the normalization constant p and/or the kernel width w. These parameters can be changed for each kernel using the following methods. Further below, it is described how to compute the new choices of the parameters.

1. Changing kernel normalization parameter

Be $K_0$ any kernel matrix. Then $$K_p = p K_0 \quad (8)$$

defines a way to change the kernel normalization parameter.

2. Changing kernel width parameter and kernel normalization parameter

Be $K_0$ positive-valued kernel matrix with a fixed width parameter w.

$$K_{p,w} = p \exp(w \log(K_0)) \quad (9)$$

defines a way to change the kernel width w and kernel normalization parameter p where the exp and log operators apply element-wise to each element of the matrix separately. The operators are no matrix exponentials or logarithms.

These parameters can be chosen adaptively based on values obtained from features over sets of images or subimages. This has the advantage that the parameters can be chosen on the correct scale of the kernel matrix values computed over the data. This improves the classification performance.

Setting these parameter values p, w adaptively requires two inputs: a data set and a function to compute a value from this dataset.

Kernel Parameter Computation

The computation of the kernel parameters uses kernel normalization estimation functions, kernel width estimation functions kernel width and/or kernel normalization estimation datasets, described below.

1. Kernel normalization estimation functions

Be K any kernel matrix of format F×M.

$$p = \frac{\min(F, M)}{tr(K)} \quad (10)$$

$$tr(K) = \sum_{i=1}^{\min(F,M)} |\lambda_i| \quad (11)$$

where $\{|\lambda_i|, i=1, \ldots, \min(F,M)\}$ are the absolute values of the singular values of a matrix coming from a singular value decomposition.

2. Kernel normalization estimation functions: 'standard deviation in reproducing hilbert space'

Be K any kernel matrix of format F×M.

$$p = \frac{1}{\max\left(10^{-8}, \frac{tr(k)}{\min(F,M)} - \frac{1}{FM}\sum_{i,j} K_{i,j}\right)} \quad (12)$$

The constant $10^{-8}$ avoids numerical degenerations and can be replaced by another small numerical value. The operator tr(K) is defined above by equation (11).

3. Kernel normalization estimation functions: cosine angle

Given a F×M matrix K, p is in this special case a F×M matrix as well. The equations (8) and (9) are meant as element-wise multiplication of two matrices in this case.

$$p_{i,j} = \frac{1}{\max\left(10^{-8}, \sqrt{K_{ij}, K_{ij}}\right)}, \quad (13)$$

the constant $10^{-8}$ avoids numerical degenerations and can be replaced by another small numerical value.

4. Kernel width estimation functions w is chosen as mean or quantile estimator such as median of the set of values given by the matrix-log($K_0$), where the logarithm applies to every element in the matrix separately. The matrix $K_0$ has been computed using any kernel function, examples are the given kernel functions in equations (3) to (6) and using w=1 and p=1 for them.

The quantile parameter of the quantile estimator can be 0.5 corresponding to the median. Alternatively the parameter can be chosen such that the classification performance measured for example by the classification error rate is small.

5. Kernel width and kernel normalization estimation datasets

The kernel width can be computed in different way, e.g. based on training dataset, testing datasets or a mixture of both.

a) Inputs for Computing the Matrix $K_0$ for Usage in Equations (8) and (9):

Left hand side set for the i-th kernel: i-th feature of a subset of the set of all training subimages 11, 12, 13 (Number of training subimages 11, 12, 13 used for kernel computation: quantity G)

Right hand side set for the i-th kernel: same as left hand side

The advantage of this method is that it does not require re-training of classifiers because the training set kernel (see the output in Section 1.2 for its definition) does never change.

b) Kernel Parameters from Test

Left hand side set for the i-th kernel: i-th feature of a subset of the set of all testing images or subimages (Number of testing subimages 11, 12, 13 used for kernel computation: quantity N).

Right hand side set for the i-th kernel: same as left hand side.

The advantage of this method is that one can adapt kernel parameters to changing statistics of the images for which a result is to be predicted. However this method requires to recompute the training set kernel (see the output in Section 1.2 for its definition) according to equations (8) or (9) and subsequently, to re-train classifiers.

c) Kernel Parameters from Train and Test

Left hand side set for the i-th kernel: i-th feature of a subset of the set of all training and testing images or subimages (Number of training and testing subimages 11, 12, 13 used for kernel computation: quantity G+N)

Right hand side set for the i-th kernel: same as left hand side

The advantage of this method is that one can adapt kernel parameters to changing statistics if the images for which a result is to be predicted. Additionally by including features from a subset of training images one can avoid overshooting of the adaptation to features from testing images or subimages when comparing to the former method. The adaptation is more moderate than the former method and robust to outliers in the testing images or subimages. However this method also requires to recompute the training set kernel (see the output in Section 1.2 for its definition) according to equations (8) or (9) and subsequently, to re-train classifiers.

In the following the using of multiple kernels and their unequal weighting is discussed.

Using multiple features brings the advantage that each feature is computed using different parameters and therefore can capture different aspects of an input image (e.g. subimage 11, 12, 13). Note that each kernel matrix is computed from one feature signature over two sets of images.

Using multiple kernel matrices together with unequal weights for them permits the generation of an input for classification, namely the resulting weighted kernel similarity matrix between two sets of subimages 11, 12, 13, which is adapted to the varying information content of the contributing features by giving higher weights to kernels which correspond to more informative features.

When selecting kernel parameters adaptively based on a reference set, a reference set can be a subset of testing images, a subset of subimages 11, 12, 13 used during training or a combination of both.

A too small kernel width parameter is known to lead to a phenomenon called overfitting. The similarities encoded in the kernel matrix will be too sensitive to small differences in feature vectors coming from noise contained in these features.

A too large value of the kernel width parameter is known to lead to a phenomenon called underfitting. The kernel matrix will be too insensitive to larger differences in feature vectors coming from informative signal content. Both extremes lead to decreased classification performance. The signal to noise ratio is different for each kernel matrix.

Therefore optimizing/setting the kernel width parameter leads to an improvement in the classification performance.

Kernel Normalization Parameter

Given a fixed weighting of kernel matrices, a too small kernel normalization parameter p for one of the kernels leads to this one kernel having merely little influence on the resulting kernel mixture and the similarities encoded therein. Effectively this removes the mis-scaled kernel from the kernel mixture. If we assume that the mis-scaled kernel contains information useful for classification, then this results in a drop in classification performance.

A too large kernel normalization parameter for one kernel results in this one kernel dominating all other kernels in the kernel mixture. Again, if the other kernels contain useful information, then this implies a drop in classification performance as well. Supervised learning is about extracting structures from a training data set and applying them on unseen test data. During that process one has to take care that one extracts rather informative structures from training data than noise components. Noise components are structures which can be found only in the finite set of training samples and which cannot be found in/validated on the majority of test data samples.

In order to be valid the assumption that structures from training data can be transferred and applied to test data requires that all objects (e.g. sets, matrices, vectors) are computed using the same parameters and methods for training and test data.

Badly scaled kernel parameters make transfer of information from training to test data difficult because they permit the algorithm either to focus on noise components (overfitting) or they make the algorithm too insensitive to informative structures (underfitting).

Testing on Test Kernel

Now K test kernels have been computed and they have been adapted based on computed kernel parameters. Not a score, i.e. being a measure of the cancer certainty in the subimage 11, 12, 13, is calculated.

The classification stage is about classifying every subimage 11, 12, 13, this means each subimage 11, 12, 13 gets assigned a numeric value denoting the certainty of presence of cancer in this subimage 11, 12, 13. The numerical value is called output score in the following.

In the subsequent heatmap stage for each subimage 11, 12, 13 a heatmap is computed. A heatmap is an assignment providing for each pixel of the subimage 11, 12, 13 a numerical value which is the contribution of this pixel in the subimage 11, 12, 13 to the output score of the subimage 11, 12, 13. The numerical value can be represented by a color which gives rise to a heatmap.

The heatmap stage requires for computing the heatmap for one subimage 11, 13 the test kernel for that subimage 11, 12, 13, the test features, in case of bag of words features all the local features and their positions within one subimage 11, 12, 13.

Finally, the heatmaps for all subimages 11, 12, 13 get overlaid into one big heatmap of the input image.

Classification
Domain: One Subimage x
Inputs:
  L Test kernels $k_l$ with column corresponding to the features of the subimage.
  Weights for Kernels $\{\beta_l / l=1, \ldots L\}$
  further parameters ($\{\alpha_i / i=1, \ldots, I\}$,b) defining the classifier
Output:
  Output Score $f(x)$ denoting certainty of presence of cancer in the subimage x. In the following three ways are listed as examples how the output score an be computed.

$$1.\ f(x) = \sum_{i=1}^{I} \alpha_i \sum_{l=1}^{L} \beta_l k_l(x_i, x) + b$$

This method uses the multiple kernel learning output function as given for example in Kloft et al., Lp norm multiple kernel learning, Journal of Machine Learning Research, 12:953-997, March 2011).

$$2.\ f(x) = \sum_{i=1}^{I} \alpha_i \sum_{l=1}^{L} k_l^{\beta_l}(x_i, x) + b$$

The difference between this and the previous method is the way to combine the L kernels $k_l$ into one kernel during classification. The power weighting used in this method parameterizes the kernel mixture differently. It can give empirically better results sometimes. A method for generalized multiple kernel learning is described in Manik Varma and Bodla Rakesh Babu. More generality in efficient multiple kernel learning. In International Conference on Machine Learning (ICML), page 134, 2009.

$$3.\ f(x) = \sum_{i=1}^{I} \sum_{l=1}^{L} \alpha_{il} k_l(x_i, x) + b$$

This method requires one weight for each kernel l and kernel row i. The first method is a special case of this method.

This can improve classification performance because each kernel and each kernel row gets a separate weight an but the number of parameters defining the classifier I×L is larger than for the first and second method I+L. This has the disadvantage of slower classification and the selection of the parameters (during training phase) is more difficult compared to the first and second method. It is known that classifier training in practice can overfit easier when there are more parameters to learn.

Learning the weights can be done during training phase via non-sparse MKL (Kloft et al., Lp multiple kernel learning, Journal of Machine Learning Research, 12:953-997, March 2011), MKL-KDA (Yan et al., Non-sparse Multiple Kernel Learning for Fisher Discriminant Analysis, Proceedings of the 2009 Ninth IEEE International Conference on Data Mining, ICDM '09, 2009, pages 1064-1069); Yan et al, Lp norm multiple kernel Fisher discriminant analysis for object and image categorization, Computer Vision and Pattern Recognition, IEEE Computer Society Conference on, 2010, pages 3626-3632) or Algorithm of Cao et al (Cao et al., Heterogeneous feature machines for visual recognition, ICCV, 2009, pages 1095-1102).

Heatmap
Domain: One Subimage x
Inputs:
  all inputs from classification stage
  L input features
  in case of input feature being a bag of word feature: all local features which belong to the bag of word feature and their positions within a subimage
Output:
  For each pixel p of the subimage x a numerical value rel(p) denoting the contribution of this pixel for the classification result $f(x)$.

In the following the details for the computation of the heatmap are given.

Learning at the level of single pixels can suffer from instability, for example caused by failed segmentation. Therefore, we derive the pixel-wise score from the prediction for a subimage 11, 12, 12 containing that pixel. Precisely, the pixel-wise score is an average of the pixel-wise scores from all subimages 11, 12, 13 which contain the pixel.

For the subimage 11, 12, 13 a set of global bag of word features over local features has been computed. Therefore we can break down the estimation of a pixel-wise score into two steps: at first by computing a dimension-wise score for each dimension of each of the bag of word features for the subimage 11, 12, 13. Then we propagate down the dimension-wise scores to all local features in the subimage 11, 12, 13 which contribute to the bag of word dimensions.

The first step can be achieved by using first order Taylor expansions of a support vector machine (SVM) prediction function.

$$f(x) = b + \sum_{i=1}^{S} \alpha_i y_i \sum_{m=1}^{K} \beta_m k_m(x_i, x) \approx f(x_0) + \langle x - x_0, \nabla_x f(x_0) \rangle$$

$$= \sum_{m=1}^{K} \sum_{d=1}^{V_m} \beta_m \left( \frac{f(x_0)}{V_m \|\vec{\beta}\|_1} + (x - x_0)^{(d,m)} \sum_{i=1}^{S} \alpha_i y_i \frac{\partial k_m}{\partial x^{(d)}}(x_0) \right)$$

$$=: \sum_{m=1}^{K} \sum_{d=1}^{V_m} r_{d,m}(x)$$

$r_{d,m}(x)$ is the relevance score for dimension d of bag of word feature m and input x which is here for notational simplicity a concatenation of all bag of word features instead of a subimage 11, 12, 13.

Since we are interested in the explanation of the prediction of our system even in the case where the prediction contradicts human experience or ground truth, we perform the Taylor expansion around a point $x_0$ which is a root of the prediction function $f(x_0)=0$. Note that for a linear kernel this expansion is exact.

In the second part we exploit the additivity in the bag of word mapping formula (0).

Assume the local feature t belongs to the bag of word feature x, part M(t)

$$R(t) := \sum_{d=1}^{V_{M(t)}} r_{d,M(t)}(x) m_d(t)$$

defines the relevance for a local feature. It is the relevance score of a bag of word dimension weighted with the bag of word contribution of the local feature to the dimension. Note that since we use soft mapping of local features to visual words (Germert et al., Kernel Codebooks for Scene Categorization, ECCV, 2008) we have in general more than one dimension d which has non-zero weights $m_d(t)$.

Finally the relevance of a pixel is the average of the relevances of all local features which contain the pixel in their support. The support of a local feature is the set of pixels from which that local feature is computed.

$$rel(p) = \frac{\sum_{t|p \in support(t)} R(t)}{\sum_{t|p \in support(t)} 1}$$

This approach shares with (Baehrens et al., How to explain individual classification decisions, Journal of Machine Learning Research, 11, pages 1803-1831, 2010) the usage of gradients in order to produce relevance scores at the level of global features. However (Baehrens et al., How to explain individual classification decisions, Journal of Machine Learning Research, 11, pages 1803-1831, 2010) does not attempt a Taylor expansion but considers the gradients $\nabla_x f(x)$ at the input point x that is to be classified. Note that the SVM prediction function is neither convex nor concave when using RBF kernels. This implies that a gradient at the prediction point does not necessarily point to the nearest point on the decision boundary. It can point in a direction which never intersects a decision boundary or to a point on the decision boundary which is far away and only limitedly representative for the prediction point x.

To see this consider a mixture with positive and negative coefficients of RBF-kernels in a one-dimensional example as shown in FIG. 3. Gradients taken at points in the intervals [−2,0] and [3.5,6] lead to local extrema instead of a root. Similarly, points on the boundaries of the depicted input interval such as −8 do not lead to a root.

This methodology to generate heatmaps here and its goals is substantially different from the correlation analysis "Visual Pattern Analyis in Histopathology Images Using Bag of Features" by Cruz-Roa et al. in Bayro-Corrochano, Eklundh (Eds.), CIAPR 2009, LNCS 5856, page 521-528, 2009, Springer. The following this article will be referred to as Caicedo et al.

Caicedo et al. build on the ground truth labels whereas we use the prediction outcome of our classifiers. Caicedo et al formulate the goal of the correlation analysis to identify the most relevant visual words for a given concept over a set of images.

In our case we want to identify the most relevant regions over the pixels of one image. We computed the heatmaps for images where no ground truth has been determined. Furthermore we did not use any cell-wise or pixel-wise ground truth for the Bag of word models.

Caicedo et al. results in a binary marking of regions which correspond to highly correlated visual word dimensions.

Our approach results in a continuous scoring for each pixel which is covered by at least one local feature.

Methodically, the visual words in Caicedo et al. are determined by computing a correlation score between the binary ground truth label of an image and the continuous value of a dimension of a Bag of word feature computed from the same image. Thresholding the correlation coefficients yields the binary marking of regions in an image. By design, this is not intended to be related to kernels or the prediction function. The domain for evaluation of correlation is a set of images.

Methodically we linearize the prediction function in terms of Bag of word feature dimensions and trace this linearization back to all local features. Our domain for evaluation is a set of local features within a single image.

In particular our approach has the advantage that we are able to mark regions accordingly which show medium to low contribution for each separate Bag of word feature however where the sum over all bag of word features yields a high contribution, even when correlation coefficients over sets of images would be low. In such a case a correlation-based analysis as done in Caicedo et al. would fail to mark these regions.

In FIG. 2 a schematic flowchart showing an embodiment of the method is shown.

Starting point is an image from a biological sample, which is automatically analyzed. respect to a pathological relevance.

In process step 100 local features from subimages 11, 12, 13 are extracted.

In process step 101 the local features of the subimage 11, 12, 13 are aggregated to a global feature of the image (1, 11, 12, 13) using a bag of visual word approach. This process step is repeated at least two times using different methods resulting in at least two bag of word feature datasets, Then in process step 102 a computation of at least two similarity measures using the bag of word features obtained from a training image dataset 103 and bag of word features from the subimage 11, 12, 13 is performed.

The image training dataset 103 comprises a set of visual words, classifier parameters, including kernel weights and bag of word features from the training images.

In process step 102 the computation of the at least two similarity measures is subject to an adaptive computation of kernel normalization parameters and/or kernel width parameters.

For each subimage 11, 12, 13 at least one score is computed in process step 104 depending on the classifier parameters and kernel weights and the at least two similarity measures, the at least one score being a measure of the certainty of one pathological category compared to the image training dataset.

In process step 105 for each pixel of the subimage 11, 12, 13 a pixel-wise score is computed using the classifier parameters, the kernel weights, the at least two similarity measures, the bag of word features of the subimage 11, 12, 13, all the local features used in the computation of the bag of word features of the subimage 11, 12, 13 and the pixels used in the computations of the local features.

At last the pixel-wise score is stored in process step 106 as a heatmap dataset linking the pixels of the image 11, 12, 13 to the pixel-wise scores.

Figure 5:
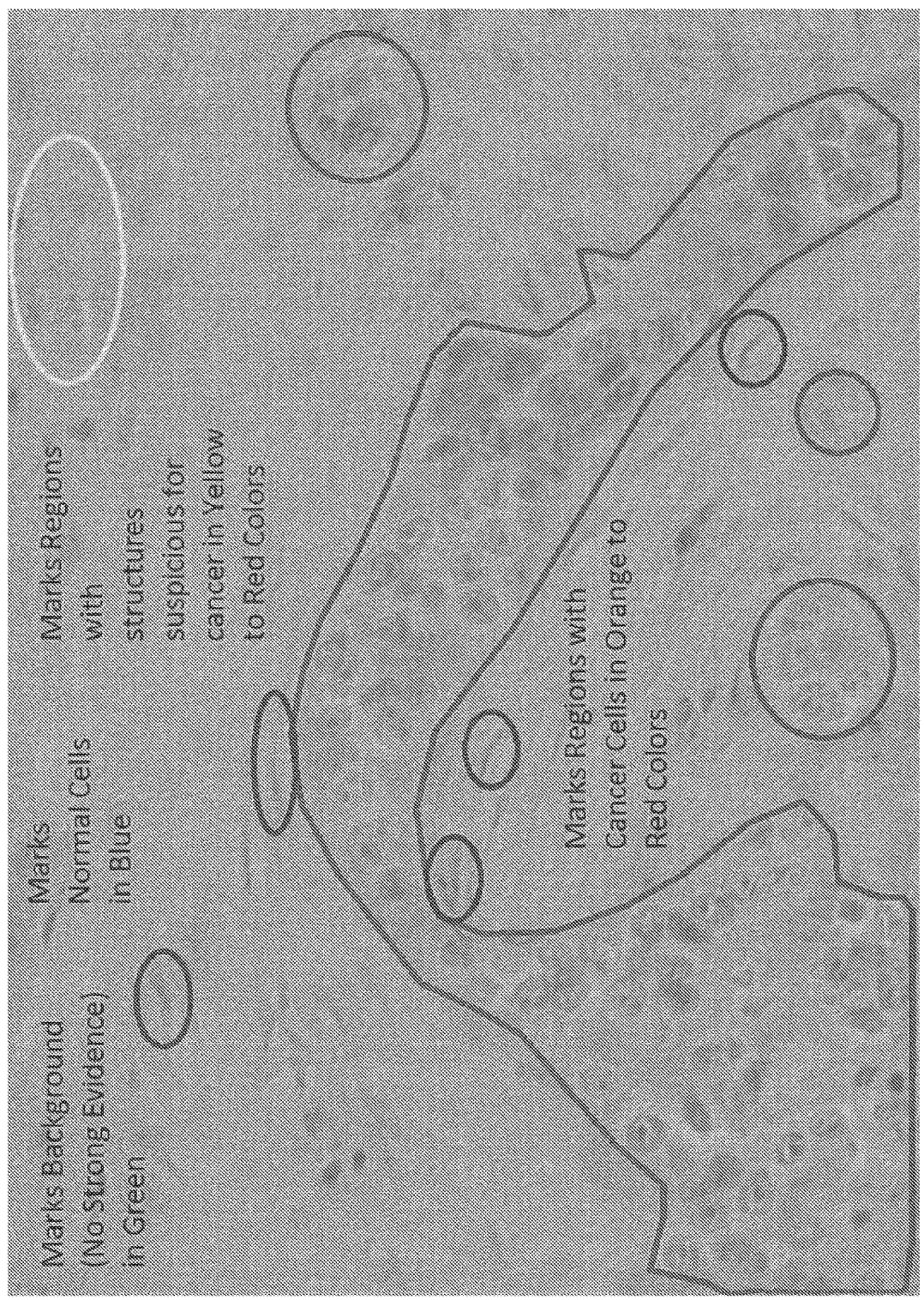
FIG. 5 a first example of a heatmap showing the certainty of cancer in an image.
Figure 6:
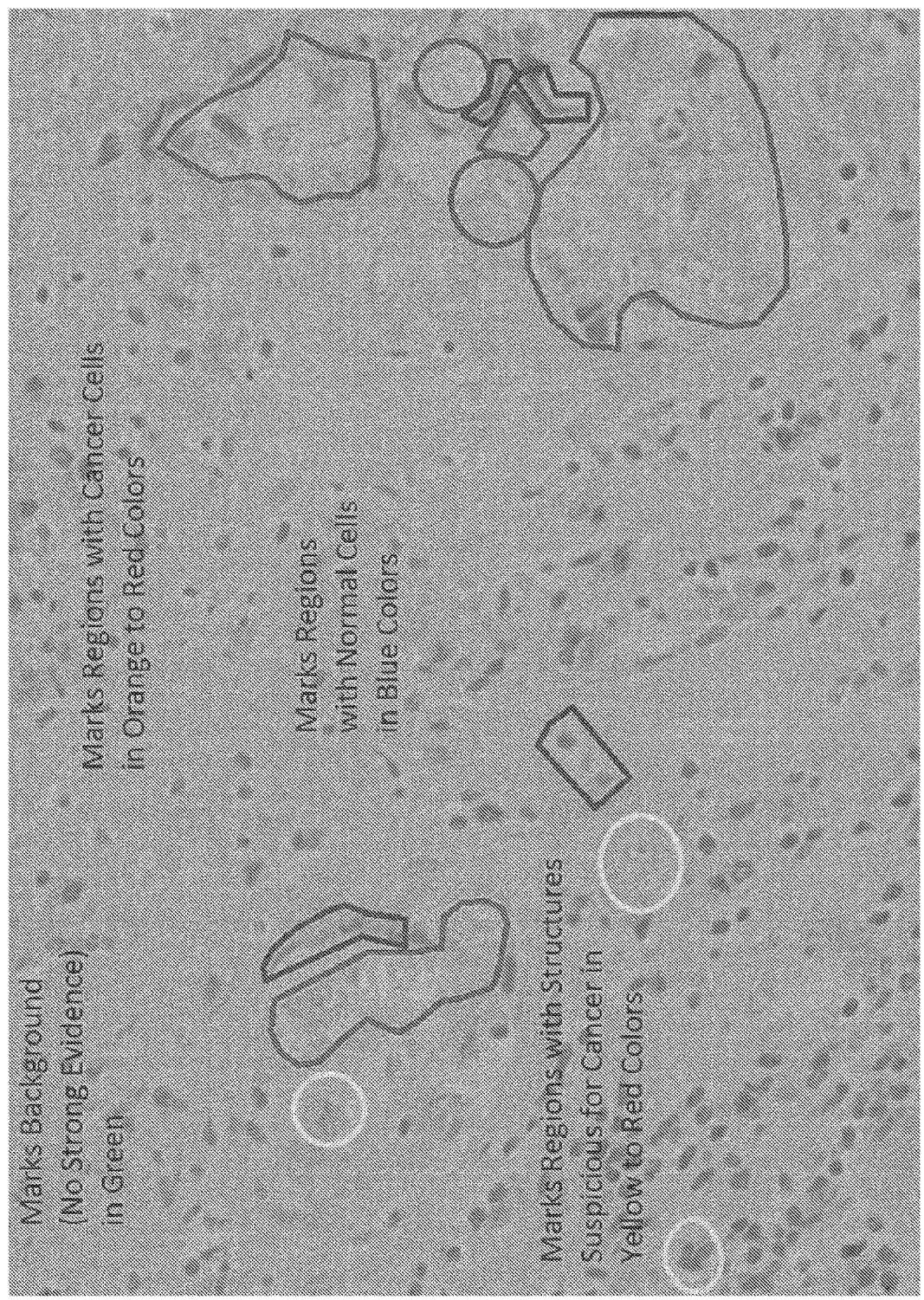
FIG. 6 a second example of a heatmap showing the certainty of cancer in an image.

In FIGS. 5 and 6 samples of heatmaps obtained by this method are given. The scores allow the ranking of regions within the image showing the prediction of certainty of cancerous structures in the image Greenish colors mark the background of the image, indicating no strong evidence, i.e. certainty for cancer. Normal cells are identified by blue markers, i.e. relatively small elliptic markers. Suspicious regions are either marked in yellow or red, indicating different levels of certainty.

In FIG. 5 five relatively small areas indicating normal cells are shown, throughout the image. In the upper right hand corner of the image a rather diffuse cluster of cells has been identified a one certainty level marked in yellow There are four regions marked in red identified with a different certainty level, including one rather large, arc-shaped region extending through the image.

FIG. 6 shows a different image in which the certainty regions have very different shapes. Three regions are marked in blue indicating normal cells. One of the normal regions is embedded in between four regions of a higher certainty.

The heatmap can provide one more opinion in case of diverging opinions by human experts, or borderline cases the heatmap explains the outcome of the classification by color-coding regions in a large image or subimage, this allows human experts to understand the results in terms of which regions of an image or subimage contribute for the classification results aggregated over subimages.

In particular the color coding can put emphasis on certain regions. This provides human experts with cues where to look in a large image or a subimage, for example in case of diverging opinions or borderline cases.

The color coding from the heatmap can serve as a second line check for medical experts whether they have considered all relevant regions in a large image.

A system using one of the embodiments described above may comprise a usual computer hardware such as a desktop computer, a notebook, a server, or network-connected sets of the above exemplary hardware types with or without graphics processing capabilities.

The system is capable to load a large input image. The system may be designed such that it allows to do certain manual preprocessing steps of the input image, for example selecting a region of the input image for analysis. This is advantageous if the input image contains samples from multiple patients, or a medical expert wants a second opinion based on a part of the input image.

Other possible automatic or manual preprocessing steps of the input image is correction of the average brightness of the input image or a selected region of it, or normalizing the distribution of pixel values in the input image or a selected region of it.

The system may be designed such that it checks for available hardware capabilities in order to determine what parts of hardware to use, for example using a GPU unit or using multiple cores on a desktop computer or notebook or using multiple CPUs on a server. The system may be designed such that it allows to select which hardware capabilities to use after checking for them. Please note here that processing of subimages can be processed independently up to the point of computing the heatmap for each subimage.

The system may be designed such that it allows to select one of several sets of parameters for classifying the input image or subimages created from it and computing heatmaps for them. Each set of parameters requires its own training dataset.

The system may be designed such that it allows to save the results which are the numerical values for certainty for the image or subimages and the resulting heatmaps on storage media such as hard disks, usb sticks, tapes or network-based storage solutions.

The examples in FIGS. 5 and 6 show the use of a particular color is demonstrated. For images stained by Haemtoxylin, a color channel combination with two color channels is advantageous, namely: grey (pixel-wise value (red+green+blue)/3) and opponent color two (pixel-wise value ((red+green-2blue)+2)/4).

The Haematoxylin stain stains in shades of blue. The difference between red and green color per pixel contains no useful information. Therefore we use as the first channel the grey color channel which captures the absolute staining intensity and the opponent color 2 channel which captures the amount of blue color in a way that is invariant to adding a constant value to the red, green and blue value of one pixel simultaneously. Toosee this add a constant c to the opponent color channel 2 defined above. The value will not change.

This invariance makes subsequent feature extraction more robust against changes in illumination during creation of images.

The embodiments of the method and the system can be used in the diagnosis or treatment of cancer or neurological disease using PET scans of the brain.

Other sources of images can originate from an analysis of inflammated tissue; CT scans, MRI scans; combination images from the above such as PET+MRI fusion. But biological sample also include samples of immobilized body liquids such as blood, cerebrospinal fluid, urine, bile, ejaculate, saliva, blood serum, lymph, mucus, peritoneal fluid, pleural fluid, gastric juice, tears, vaginal secretion. All these body fluid can provide diagnostical information.

1 Image
11 Subimage
12 Subimage
13 Subimage
21 Region
22 Region

APPENDIX AS PART OF THE SPECIFICATION

In the following appendix further embodiments of the invention are briefly discussed.

In particular equation (6) is an alternative for he relevance of local features.

Equation (8) is an alternative for the relvances of individual pixels of a tile. The norm is not used in this case.

Equation (6) refers to a special handling of "0/0" cases defined as 0 in equation (4). In equation (4) the expression "0/0" can be defined as 0.

Equation (5) is an explanation for equations (4) and (6). The idea is that the relevances R(l) of all local features should sum to the Taylor approximation of the SVM and/or MKL prediction function.

1 BoW

The mappings of all local features to the visual words are aggregated into one histogram which constitutes the BoW feature and the histogram gets normalized.

This can be expressed formally as $$x_d = \frac{1}{N}\sum_{i=1}^{N} m_d(l_i) \text{ s.t. } \sum_d m_d(l_i) \leq 1 \quad (1)$$

2 heatmap

The first step can be achieved by using first order Taylor expansions of the SVM prediction function which yield a linearization $r_{d,u}(x)$ of the SVM prediction $f(x)$ for the BoW features x of the subimage.

$$f(x) = b + \sum_{i=1}^{S} \alpha_i y_i \sum_{m=1}^{K} \beta_m k_m(x_i, x) \approx f(x_0) + \langle x - x_0, \nabla_x f(x_0)\rangle \quad (2)$$

$$= \sum_{m=1}^{K}\sum_{d=1}^{V_m} \beta_u \left( \frac{f(x_0)}{V_m\|\vec{\beta}\|_1} + (x - x_0)^{(d,m)} \sum_{i=1}^{S} \alpha_i y_i \frac{\partial k_m(x_i, \cdot)}{\partial x^{(d)}}(x_0) \right)$$

$$=: \sum_{m=1}^{K}\sum_{d=1}^{V_m} r_{d,m}(x)$$

$$r_{d,m}(x) := \beta_u \left( \frac{f(x_0)}{V_m\|\vec{\beta}\|_1} + (x - x_0)^{(d,m)} \sum_{i=1}^{S} \alpha_i y_i \frac{\partial k_m(x_i, \cdot)}{\partial x^{(d)}}(x_0) \right) \quad (3)$$

$r_{d,m}(x)$ is the relevance score for dimension d of BoW feature part m and input x which is a concatenation of all BoW features used. Since we are interested in the explanation of the prediction of our system even in the case where the prediction contradicts human experience or ground truth, we perform the Taylor expansion around a point $x_0$ which is a root of the prediction function $f(x_0)=0$. Note that for a linear kernel this expansion is exact.

In the second part we exploit the additivity in the BoW mapping formula (1). Assume the local feature l belongs to the BoW feature x, part M(l). Please note that $m_d$ here does not refer to a BoW feature part as in the equation above but to a mapping function of local features onto the d-th visual word. Be i other local features belonging to the same BoW feature part and to the same image as the local feature l: M(i)=M(l)

$$R(l) := \sum_{d=1}^{V_{M(l)}} r_{d,M(l)}(x) \frac{m_d(l)}{\sum_{i|M(i)=M(l)} m_d(i)} \quad (4)$$

defines the relevance for a local feature l. We assume here 0/0-terms to be defined as zero. R(l) is equal to the relevance score of a BoW dimension weighted with the BoW contribution of the local feature to the dimension. Note that since we use soft mapping of local features to visual words we have in general for each local feature l more than one dimension d which has non-zero weights $m_d(l)\neq 0$. Furthermore note that the summation $\Sigma_{i|M(i)=M(l)}(\cdot)$ is performed over all local features i from the same image as the local feature l Formula 4 has the property that summing over all local features yields the value the Taylor approximation $\Sigma_{u=1}^{K}\Sigma_{d=1}^{V_u} r_{d,u}(x)$ of the SVM prediction.

This property is the justification for the definition of the relevance of a local feature according to equation (4).

$$\sum_l R(l) = \sum_l \sum_{d=1}^{V_{M(l)}} r_{d,M(l)}(x) \frac{m_d(l)}{\sum_{i|M(i)=u} m_d(i)} \quad (5)$$

$$= \sum_{u=1}^{K} \sum_{d=1}^{V_u} \sum_{l|M(l)=u} r_{d,M(l)}(x) \frac{m_d(l)}{\sum_{i|M(i)=M(l)} m_d(i)}$$

$$= \sum_{u=1}^{K} \sum_{d=1}^{V_u} r_{d,u}(x) \sum_{l|M(l)=u} \frac{m_d(l)}{\sum_{i|M(i)=u} m_d(i)}$$

$$= \sum_{u=1}^{K} \sum_{d=1}^{V_u} r_{d,u}(x)$$

In the case that $$Z_k(x) = \left\{ d \ \Big| \ \sum_{i|M(i)=k} m_d(i) = 0 \right\}$$

is non-empty for k=M(l), the above equation (5) yields only a lower bound because it will have terms being defined as zero in cases of 0/0. For this case there exists an alternative to equation (4) which asserts equality in equation (5) again.

$$R(l) := \sum_{d=1}^{V_{M(l)}} r_{d,M(l)}(x) \frac{m_d(l)}{\sum_{i|M(i)=M(l)} m_d(i)} + \frac{\sum_{d \in Z_{M(l)}(x)} r_{d,M(l)}(x)}{\sum_{i|M(i)=M(l)} 1} \quad (6)$$

The idea is that the accumulated values of $r_{d,M(l)}(x)$ for $d \in Z_{M(l)}$ are evenly distributed to all local features l belonging to BoW feature part M(l). Note that $d \in Z_k$ means that the relevance $r_{d,k}$ for BoW dimension d is never used by any local feature used for computation of BoW feature part k in formula (4).

Finally the relevance of a pixel is the sum of the relevances scores over all local features which cover that pixel taken from one subimage.

This can be averaged over the local features covering a pixel:

$$\text{rel}(p) = \frac{\sum_{l|p \in \text{support}(l)} R(l)}{\sum_{l|p \in \text{support}(l)} 1} \quad (7)$$

or without averaging:

$$\text{rel}(p) = \sum_{l|p \in \text{support}(l)} R(l) \quad (8)$$

There may be no need to average over all local features like in equation (7), because the normalization in formula 4 is able to adjust for oversampling of a pixel by local features taken from within one subimage.

The invention claimed is:

1. A method for the automatic analysis of an image of a biological sample with respect to a pathological relevance, wherein
   a) local features of the image are aggregated to a global feature of the image using a bag of Visual word approach,
   b) step a) is repeated at least two times using different methods resulting in at least two bag of word feature datasets,
   c) computation of at least two similarity measures using the bag of word features obtained from a training image dataset and bag of word features from the image, the image training dataset comprising a set of Visual words, classifier parameters, including kernel weights and bag of word features from the training images,
   the computation of the least to two similarity measures based on one of the following kernels:
   Generalized exponential kernel $$k_{w,p}(x_l, x_r) = p\exp(-wd((x_l, x_r)))  \quad (3),$$

Gaussian kernel $$k_{w,p}(x_l, x_r) = p\exp(-w\|x_l - x_r\|_2^2) \quad (4),$$

Chi2 kernel $$k_{w,p}(x_l, x_r) = p\exp\left(-w \sum_{d \in \{1,\ldots,D\} | x_l^{(d)} + x_r^{(d)} > 0} \frac{(x_l^{(d)} - x_r^{(d)})^2}{x_l^{(d)} + x_r^{(d)}}\right) \quad (5)$$

Polynomial kernel $$k_{w,p,t}(x_l, x_r) = p(\langle x_l, x_r \rangle + w)^t \quad (6)$$

d) the computation of the at least two similarity measures is subject to an adaptive computation of kernel normalization parameters and/or kernel width parameters,
   e) for each image at least one score is computed depending on the classifier parameters and kernel weights, wherein this computation is performed in two steps:
   at first by computing a dimension-wise score for each dimension of each of the bag of word features for a subimage by using first order Taylor expansions of a support vector machine prediction function around a point $x_0$ which is a root of the prediction function $f(x_0)=0$:

$$f(x) = b + \sum_{i=1}^{S} \alpha_i y_i \sum_{m=1}^{K} \beta_m k_m(x_i, x) \approx f(x_0) + \langle x - x_0, \nabla_x f(x_0) \rangle$$

$$= \sum_{m=1}^{K} \sum_{d=1}^{V_m} \beta_m \left( \frac{f(x_0)}{V_m \|\beta\|_1} + (x - x_0)^{(d,m)} \sum_{i=1}^{S} \alpha_i y_i \frac{\partial k_m}{\partial x^{(d)}}(x_0) \right)$$

$$=: \sum_{m=1}^{K} \sum_{d=1}^{V_m} r_{d,m}(x)$$

with $r_{d,m}(x)$ as the relevance score for dimension d of bag of word feature m and input x which is here for notational simplicity a concatenation of all bag of word features instead of a subimage, in a second step exploiting the additivity in the bag of word mapping formula $$x_d = \sum_{i=1}^{N} m_d(l_i), \quad (0)$$

and assuming the local feature t belongs to the bag of word feature x, part M(t), with $$R(t) := \sum_{d=1}^{V_{M(t)}} r_{d,M(t)}(x) m_d(t)$$

defining the relevance for a local feature, being the relevance score of a bag of word dimension weighted with the bag of word contribution of the local feature to the dimension,
   then the relevance of a pixel is the average of the relevances of all local features which contain the pixel in their support, the support of a local feature is the set of pixels from which that local feature is computed $$\text{rel}(p) = \frac{\sum_{t|p \in \text{support}(t)} R(t)}{\sum_{t|p \in \text{support}(t)} 1}$$

and the at least two similarity measures, the at least one score being a measure of the certainty of one pathological category compared to the image training dataset, for each pixel of the image the pixel-wise score (rel(p)) is computed using the classifier parameters ($\alpha$), the kernel weights ($\beta$), the at least two similarity measures ($k_m$), the bag of word features ($m_d$) of the image, all the local features used in the computation of the bag of word features of the image and the pixels used in the computations of the local features,
   f) the pixel-wise score is stored as a heatmap dataset linking the pixels of the image to the pixel-wise scores, wherein the scores for the region of the digitized image are annotated to an output image for analysis visually of the degree of certainty of abnormal cell activity during the diagnosis and treatment of pathological deviations.

2. The method according to claim 1, wherein a basis pixel for defining a region is determined by a biased sampling approach, a grid sampling approach and/or an overlapping grid sampling approach.

3. The method according to claim 1, wherein local features are computed with a scale-invariant feature transform, a pixel-wise intensity quantile estimator vector method, a pixel wise gradient norm quantile estimator vector method, a method using pixel wise intensity histograms and/or method using pixel wise gradient norm histograms.

4. The method according to claim 1, wherein the calculation of a bag of words from the local features of the subimages uses a method for soft mapping, a method for soft mapping with rank and/or a method for soft mapping with adaptive exponent.

5. The method according to claim 1, wherein the image is a subimage taken from an image of a biological sample.

6. The method according to claim 1, wherein the images and/or subimages comprise details at approximately the same scale and/or the same color channel.

7. The method according to claim 1, wherein at least one kernel is a linear kernel, a generalized exponential kernel, a Gaussian kernel, a chi2kernel, a polynomial kernel or a histogram intersection kernel.

8. The method according to claim 1, wherein for at least one kernel parameter, especially a kernel width and/or a kernel normalization parameter an adaptive estimation is performed.

9. The method according to claim 1, wherein a training image dataset is generated from a set of subimages together with a binary label for each of them indicating whether a certain medical condition, especially for example cancer cells, structures indicating an ongoing inflammation process, is visible or not, by
   a) computing a set of local features from the set of training images,
   b) computing visual words from the set of local features,
   c) computing bag of words features from the set of training images using the visual words and the local features from each image,
   d) computing training kernels from the bag of words features,
   e) computing adaptive parameters for the kernels and adapting the kernels to these parameters,
   f) training a classifier on the kernels in order to obtain classifier parameters.

10. The method according to claim 1, wherein visual words are computed by k-means and/or ERCF.

11. The method according to claim 1, wherein for images stained by Haematoxylin, a color channel combination with two color channels, namely: grey (pixel-wise value (red+green+blue)/3) and opponent color two (pixel-wise value ((red+green−2blue)+2)/4) is used.

12. The method according to claim 1, wherein biased random sampling is used for the generation of regions for local feature extraction.

13. The method according to claim 1, wherein at least one set of parameters defining a classifier is learned
   a) using weights $\beta_1$ constant for all kernels and then applying an support vector machine or,
   b) $L_p$ norm multiple kernel learning or non-sparse multiple kernel learning for Fisher Discriminant Analysis or,
   c) using a generalized multiple kernel learning or,
   d) using a heterogenous feature machine for visual recognition.

14. The method according to claim 1, wherein the assignment of bag of words is generated from soft mapping "rank" approach using additionally an exponent parameter and computing the ranks of distances of a local feature to the set of visual words and/or a soft mapping including an adaptive exponent approach using the local feature l to compute distances of that local feature to the visual words, especially choosing the parameter $\sigma(l)$ adaptively such that the mapping value for the nearest visual word relative to the given local feature is $1/v$ times larger than the mapping value for the N-nearest visual word.

15. The method according to claim 1, wherein local features are computed by at least one of the following methods over transformations of the color channels in the input image:
   a) Gradient-based descriptor underlying the scale-invariant feature transform (SIFT),
   b) vectors of quantile estimators defined by sets of quantile parameters using pixel-wise intensities taken from the subimage,
   c) vectors of quantile estimators defined by sets of quantile parameters using pixel-wise norms of gradients taken from the subimage,
   d) a method using histograms of pixel-wise intensities,
   e) method using histograms of pixel-wise gradient norm,
   f) a combination of b) and c),
   g) a combination d) and e).

16. A system for the automatic analysis of an image of a biological sample with respect to a pathological relevance with means for performing the method according to claim 1.

* * * * *